United States Patent
Bard et al.

(10) Patent No.: US 9,442,117 B2
(45) Date of Patent: Sep. 13, 2016

(54) METHOD FOR THE DETECTION OF BIOLOGICAL MOLECULES USING A TWO PARTICLE COMPLEX

(71) Applicant: Board of Regents of the University of Texas System, Austin, TX (US)

(72) Inventors: Allen J. Bard, Austin, TX (US); Wujian Miao, Hattiesburg, MS (US)

(73) Assignee: Board of Regents of the University of Texas System, Austin, TX (US)

( * ) Notice: Subject to any disclaimer, the term of this patent is extended or adjusted under 35 U.S.C. 154(b) by 31 days.

(21) Appl. No.: 14/465,326

(22) Filed: Aug. 21, 2014

(65) Prior Publication Data

US 2015/0044669 A1 Feb. 12, 2015

Related U.S. Application Data

(60) Division of application No. 13/457,086, filed on Apr. 26, 2012, now Pat. No. 8,871,917, which is a continuation of application No. 11/159,412, filed on Jun. 23, 2005, now Pat. No. 8,188,243.

(60) Provisional application No. 60/581,719, filed on Jun. 23, 2004.

(51) Int. Cl.
  C12Q 1/68 (2006.01)
  G01N 33/58 (2006.01)
  G01N 33/532 (2006.01)
  G01N 33/543 (2006.01)

(52) U.S. Cl.
  CPC .......... *G01N 33/582* (2013.01); *C12Q 1/6802* (2013.01); *C12Q 1/6816* (2013.01); *C12Q 1/6825* (2013.01); *C12Q 1/6834* (2013.01); *C12Q 1/6837* (2013.01); *G01N 33/532* (2013.01); *G01N 33/54313* (2013.01); *G01N 33/54373* (2013.01)

(58) Field of Classification Search
  None
  See application file for complete search history.

(56) References Cited

U.S. PATENT DOCUMENTS

| | | |
|---|---|---|
| 5,182,016 A | 1/1993 | Funkenbusch et al. |
| 5,336,596 A | 8/1994 | Bronstein et al. |
| 5,369,036 A | 11/1994 | Mercolino et al. |
| 5,500,188 A | 3/1996 | Hafeman et al. |
| 5,571,711 A | 11/1996 | van der Bruggen et al. |
| 5,589,334 A | 12/1996 | Coulie et al. |
| 5,599,889 A | 2/1997 | Stover et al. |
| 5,610,013 A | 3/1997 | Van den Eynde et al. |
| 5,679,519 A | 10/1997 | Oprandy |
| 5,714,089 A | 2/1998 | Bard et al. |
| 5,731,089 A | 3/1998 | Kunikiyo et al. |
| 5,792,621 A | 8/1998 | Verostko et al. |
| 5,821,122 A | 10/1998 | Guilloux et al. |
| 5,935,779 A * | 8/1999 | Massey .................. C07H 21/00 435/6.11 |
| 5,935,818 A | 8/1999 | Israeli et al. |
| 5,939,526 A | 8/1999 | Gaugler et al. |
| 6,037,124 A | 3/2000 | Matson |
| 6,096,500 A | 8/2000 | Oprandy et al. |
| 6,136,268 A | 10/2000 | Ala-Kleme et al. |
| 6,140,045 A | 10/2000 | Wohlstadter et al. |
| 6,140,138 A | 10/2000 | Bard et al. |
| 6,217,868 B1 | 4/2001 | Wallace et al. |
| 6,271,041 B1 | 8/2001 | Leland et al. |
| 6,312,896 B1 | 11/2001 | Heroux et al. |
| 6,316,607 B1 | 11/2001 | Massey et al. |
| 6,319,670 B1 | 11/2001 | Sigal et al. |
| 6,325,973 B1 | 12/2001 | Leland et al. |
| 6,524,865 B1 | 2/2003 | Martin et al. |
| 6,548,264 B1 | 4/2003 | Tan et al. |
| 6,706,861 B2 | 3/2004 | Singh et al. |
| 6,808,939 B2 | 10/2004 | Sigal et al. |
| 6,846,629 B2 | 1/2005 | Sigal et al. |
| 6,881,536 B1 | 4/2005 | Shah et al. |
| 7,176,036 B2 | 2/2007 | Wang et al. |
| 7,524,630 B2 | 4/2009 | Tan et al. |
| 7,741,033 B2 | 6/2010 | Kelley et al. |
| 8,188,243 B2 | 5/2012 | Bard et al. |
| 2001/0018194 A1* | 8/2001 | Terpetschnig ......... B82Y 15/00 435/7.92 |
| 2003/0118477 A1 | 6/2003 | Liljestrand et al. |
| 2003/0215845 A1 | 11/2003 | Bille |
| 2004/0058389 A1 | 3/2004 | Wang et al. |
| 2004/0067503 A1 | 4/2004 | Tan et al. |
| 2004/0253624 A1 | 12/2004 | Smith et al. |
| 2004/0259148 A1 | 12/2004 | Sigal et al. |
| 2005/0136497 A1 | 6/2005 | Tsionsky et al. |
| 2006/0078912 A1 | 4/2006 | Bard et al. |

FOREIGN PATENT DOCUMENTS

| | | |
|---|---|---|
| CA | 1339465 | 9/1997 |
| JP | 06-300763 | 10/1994 |
| JP | 09-184841 | 7/1997 |
| JP | 2004-361334 | 12/2004 |
| WO | WO-92/14139 A1 | 8/1992 |
| WO | WO-92/20356 | 11/1992 |
| WO | WO-94/14459 | 7/1994 |
| WO | WO-94/21126 | 9/1994 |
| WO | WO-95/00159 | 1/1995 |
| WO | WO-95/03422 | 2/1995 |
| WO | WO-96/10577 | 4/1996 |
| WO | WO-96/21154 | 7/1996 |
| WO | WO-99/42618 | 8/1999 |
| WO | WO-03/089906 | 10/2003 |

OTHER PUBLICATIONS

U.S. Appl. No. 60/374,405, filed Apr. 22, 2002, Weihong.

(Continued)

*Primary Examiner* — Prabha Chunduru
(74) *Attorney, Agent, or Firm* — Foley & Lardner LLP

(57) ABSTRACT

Methods, compositions and kits for detecting analytes of interest in a sample using electrogenerated chemiluminescence are provided. Compositions comprising at least one solid support that entraps or contains an electrogenerated chemiluminescent moiety also provided.

21 Claims, 18 Drawing Sheets

(56) References Cited

OTHER PUBLICATIONS

Barnett, N.W. et al., "Synthesis and Preliminary Analytical Evaluation of the Chemiluminescence from (4-[4-)dichloromethylsilanyl)-butyl]-4'-methyl-2,2'-bipyridyl)bis(2,2'-bipyridyl)ruthenium(II) Covalently Bonded to Silica Particles" Analyst 127:455-58 (2002).
Boom et al., "Rapid and Simple Method for Purification of Nucleic Acids," J. Clin.Microbiol., 28:495-503 (1990).
Christodoulides et al., "A Microchip-Based Multianalyte Assay System for the Assessment of Cardiac Risk," Anal. Chem., 74:3030-36 (2002).
Debad et al., "Clinical and Biological Applications of ECL" in Electrogenerated Chemiluminescence, (A. J. Bard ed., Marcel Dekker 2004), Chapter 8, pp. 359-396.
Fernandez et al., "Transverse Relaxation-Optimized NMR Spectroscopy with the Outer Membrane Protein OmpX in Dihexanoyl Phosphatidylcholine Micelles," Proc. Natl. Acad. Sci., 98:2358-63 (2001).
Haight, "Generalizations of the Poisson Distribution," Handbook of the Poisson Distribution, (John Willey & Sons, Inc., 1967), Chapter 3, pp. 30-81.
Harrison et al., "Development of a Novel Photoreactive Calmodulin Derivative: Cross-Linking of Purified Adenylate Cyclase from Bovine Brain," Biochemistry, 28: 6023-27 (1989).
He, X. et al., "Photostable Luminescent Nanoparticles as Biological Label for Cell Recognition of System Lupus Erythematosus Patients" J. Nanosci. Nanotech. 2:317-20 (2002).
International Search Report and written opinion dated Oct. 5, 2006, from PCT application PCT/US2005/022388.
Janeway et al., Immunobiology, (5th ed. Garland Publishing 2001), pp. 619-621.
Kenten et al., "Improved Electrochemiluminescent Label for DNA Probe Assays: Rapid Quantitative Assays of HIV-1 Polymerase Chain Reaction Products," Clin. Chem.,38:873-79 (1992).
Kenten et al., "Rapid Electrochemiluminescence Assays of Polymerase Chain Reaction Products", Clinical Chemistry, vol. 37, No. 9, pp. 1626-1632 (1991).
Kurn, "Luminescence Oxygen Channeling Assay (LOCI(TM)): A Highly Sensitive and Versatile Homogenous Assay Method," in Novel Approaches in Biosensors and Rapid Diagnostic Assays, (Z. Liron et al., Plenum Publishers 2001), pp. 265-272.
Leland et al., "Electrogenerated Chemiluminscence: An Oxidative-Reduction Type ECL Reaction Sequence Using Tripropyl Amine," J. Electrochem. Soc., 137:3127-31 (1990).
Lelkes et al., "Interaction of French-Pressed Liposomes with Isolated Bovine Adrenal Chromaffin Cells," J. Biol. Chem., 260:1796-803 (1985).
Lund et al., "Assessment of Methods for Covalent Binding of Nucleic Acids to Magnetic Beads, DynabeadsTM, and the Characteristics of the Bound Nucleic Acids in Hybridization Reactions," Nucleic Acids Res., 16:10861-80 (1988).
Maysinger et al., "Block Copolymers Modify the Internalization of Micelle-Incorporated Probes into Neural Cells," Biochim. Biophys. Acta., 1539:205-17 (2001).
Mcintyre et al., "Charge Transfer Reaction Inverse Photoemission Spectroscopy(CTRIPS)," J. Electroanal. Chem., 196:199-202 (1985).
Mcintyre et al., "Charge Transfer Reaction Inverse Photoemission Spectroscopy(CTRIPS)," J. Electroanal. Chem., 228:293-300 (1987).
Mcintyre et al., "Inverse-Photoemission Spectroscopy at the Metal-Electrolyte Interface," Phys. Rev. Lett., 56:651-54 (1986).
Miao et al., "Electrogenerated Chemiluminescence. 72. Determination of Immobilized DNA and C-Reactive Protein on Au(111) Electrodes Using Tris(2,2'-bipyridyl)ruthenium(II) Labels," Anal. Chem., 75:5825-34 (2003).
Miao et al., "Electrogenerated Chemiluminescence 69: The Tris(2,2'-bipyridine)ruthenium(II), (Ru(bpyh2 )/Tri-n-propylamine (TPrA) System Revisited—A New Route Involving TPrA Cation Radicals," J. Am. Chem. Soc., 124:14478-85 (2002).
Miao et al., "Electrogenerated Chemiluminescence. 77. DNA Hybridization Detection at High Amplification with [Ru(bpy)3]2-Containing Microspheres," Anal. Chem.,76:5379-86 (Sep. 2004).
Miao et al., "Electrogenerated Chemiluminescence. 80. C-Reactive Protein Determination at High Amplification with [Ru(bpy)3]2-Containing Microspheres," Anal. Chem., 76:7109-13 (Dec. 2004).
Min et al., "Highly Sensitive and Specific Detection of Viable *Escherichia coli* in Drinking Water," Anal. Biochem., 303:186-93 (2002).
Murakoshi et al., "Observation and Mechanism of Photon Emission at Metal-Solution Interfaces," Phys. Rev. B Condens. Matter, 47:2278-88 (1993).
Murakoshi et al., "Photon Emission at the Metal/Acetonitrile Solution Interface: Effects of Redox Species and Electrode Metal," J. Phys. Chem., 96:4593-98 (1992).
Nelson et al., "Validation of Probe EFD52 (D17S26) for Forensic DNA Analysis," J. Forensic Sci., 41 :557-68 (1996).
Nielson et al., "Peptide Nucleic Acid: A Versatile Tool in Genetic Diagnostics and Molecular Biology," Cur. Op. Biotech, 12:16-20 (2001).
Ouyang et al., "Inverse Photoemission Spectroscopy at Metal/Acetonitrile Interface by Hole Injection through Solution Species," J. Phys. Chem., 92:5201-05 (1988).
Ouyang et al., "Inverse Photoemission Spectroscopy at the PUAcetonitrile Interface with Several Redox Couples," J. Phys. Chem., 91 :4058-62 (1987).
Palmer et al., 2,2'-Bipyridine Complexes, Inorganic Chemistry, vol. 5, No. 5, May 1966, pp. 864-878.
PCT International Preliminary Report on Patentability dated Jan. 11, 2007, from PCT application PCT/US2005/022388.
Penchovsky et al., "End-Specific Covalent Photo-Dependent 1mmobilisation of Synthetic DNA to Paramagnetic Beads," Nucleic Acids Res., 28(e98):1-6 (2000).
Pollice et al., "Use of Nonradioactive DNA Probes for the Detection of Infectious Bacteria," Clin. Lab. Med., 5:463-73 (1985).
Rigaud et al., "Mechanisms of Membrane Protein Insertion into Liposomes during Reconstitution Procedures Involving the Use of Detergents. 2. Incorporation of the Light-Driven Proton Pump Bacteriorhodopsin," Biochemistry, 27:2677-88 (1988).
Riguad et al., "Liposomes as Tools for the Reconstitution of Biological Systems" in Liposomes as Tools in Basic Research and Industry, (philippot and Schuber eds., CRC Press, (1995) pp. 71-88.
Santra S. et al., "Conjugation of Biomolecules with Luminophore-Doped Silica Nanoparticles for Photostable Biomarkers", Anal. Chem. 2001, vol. 73 pp. 4988-4993.
Santra, S. et al., "Development of Novel Dye-doped Silica Nanoparticles for Biomarker Application" J. Biomed. Optics 6:160-66 (2001).
Savic et al., "Micellar Nanocontainers Distribute to Defined Cytoplasmic Organelles," Science, 300:615-18 (2003).
Uosaki et al., "Charge Transfer Reaction Inverse Photoemission Spectroscopy (CTRIPS) at a Gold/Acetonitrile Solution Interface. Evidence for Photon Emission via Surface States," Chem. Letters, 7:1159-62 (1990).
Uosaki et al., "Photon Emission via Surface State at the Gold/Acetonitrile Solution Interface," J. Phys. Chem., 95:779-83 (1991).
Velan, et al., "Screening Recombinant DNA Libraries" in Current Protocols in Molecular Biology, (F. M. Ausubel ed., Greene Publishing Associates and Wiley Interscience, 1989), Chapter 6, pp. 6.0.1-6.8.5.
Wang et al., "'Electroactive Beads' for Ultrasensitive DNA Detection," Langmuir, 19:989-991 (2003).
Wilchek et al., "Biotin-Containing Reagents" in Methods in Enzymology, 184:123-240 (1990).

(56) References Cited

OTHER PUBLICATIONS

Willner et al., "Layered Functionalized Electrodes for Electrochemical Biosensors Applications" in Biosensors and Their Applications (Yang and Ngo eds., Plenum Pulishers 2000), Chapter 4, pp. 47-98.

Wrigglesworth et al., "Dynamics of Proteoliposome Formation," Biochem J., 246:737-44 (1987).

Yoon et al., "Development of a Membrane Strip Immunosensor Utilizing Ruthenium as an Electro-chemiluminescent Signal Generator," Biosensors & Bioelectronics 19:289-96 (2003).

Zhao et al., "Ultrasensitive DNA Detection using Highly Fluorescent Bioconjugated Nanoparticles," J. Am. Chem. Soc., 125:11474-75 (2003).

\* cited by examiner (a) BLUE, EXPOSURE TIME 2s  (b) YELLOW~ORANGE (5s)  (c) WEAK GREEN (19s)

METHOD FOR THE DETECTION OF BIOLOGICAL MOLECULES USING A TWO PARTICLE COMPLEX

CROSS-REFERENCE TO RELATED APPLICATIONS

This patent application is a divisional of U.S. application Ser. No. 13/457,086, filed on Apr. 26, 2012, which is a continuation of U.S. application Ser. No. 11/159,412, filed on Jun. 23, 2005, which claims the benefit of U.S. Provisional Patent Application 60/581,719, filed on Jun. 23, 2004; the entire contents of which are hereby incorporated by reference, for any and all purposes.

BACKGROUND

There is a continuous and expanding need for rapid, highly specific methods of detecting and quantifying analytes such as chemical, biochemical, and biological substances. In particular, methods for measuring small quantities of pharmaceuticals, metabolites, biological markers, microorganisms, viruses and other pathogens are desired. The presence of these materials can often be determined by binding methods which exploit the high degree of specificity which characterizes many biological systems. Known methods which rely on binding to detect a molecule of interest present in a sample include nucleic acid hybridization techniques and protein-ligand interactions such as antibody-antigen binding. In these methods, the existence of a complex of diagnostic value is typically indicated by the presence/activation or absence/deactivation of an observable label which has been attached to one or more of the materials comprising the complex.

Sensitivity and selectivity are both desirable attributes of any system for detecting specific molecules of interest present in a sample comprised of a plurality of components. Sensitivity, in DNA hybridization and other bioassays for the detection of biological molecules of interest, is important in clinical diagnostics (Liron and Fisher Eds. Novel Approaches in Biosensors and Rapid Diagnostic Assays, Kluwer Academic/Plenum Publishers: New York, 2000; Kenton et al. 1992, Clin. Chem. 38:873; Chistodoulides et al. 2002, Anal. Chem. 74:3030), forensic chemistry (Heller, 2002, Annu. Rev. Biomed. Eng. 4:129; Nelson et al. 1996, J. Forensic Sci. 41:557), environmental investigations (Lucarelli et al. 2002, Talanta 56:949; Min et al. 2002, Anal. Biochem. 303:186), pharmaceutical studies (Heller, 2002, Annu. Rev. Biomed. Eng. 4:129; Pollice et al. 1985, Clin. Lab. Med. 5:463), and biological warfare agent detection (Smith, 2002, Anal. Chem. 74:462A; Miao and Bard, 2003, Anal. Chem. 75:5825). Thus any system which provides for sensitive and selective detection of molecules of interest will have broad applicability in all of these fields.

Electrochemiluminescence (ECL) methods have been widely used in binding studies, because of their high sensitivity, wide dynamic range, and selectivity (U.S. Pat. No. 6,316,607; Bard, A. J. Ed. Electrogenerated Chemiluminescence, Marcel Dekker New York, 2004). For example, a variety of techniques are available for the detection of DNA, where electrochemical, fluorescent, and ECL active labels attached to a target single stranded DNA (t-ssDNA) produce the measurable signal in the analysis process (Liron and Fisher Eds. Novel Approaches in Biosensors and Rapid Diagnostic Assays, Kluwer Academic/Plenum Publishers: New York, 2000; Yang and Ngo Eds. Biosensors and Their Applications, Kluwer Academic/Plenum Publishers: New York, 2000; Cunningham, Introduction to Bioanalytical Sensors, J. Wiley & Sons, Inc.: New York, 1998). The sensitivity of these methods is often limited since the intensity of the measured signal is generally proportional to the amount of t-ssDNA, and traditionally, only one or a few labels can be attached to one t-ssDNA. A number of approaches have been developed in which one DNA can be labeled with a larger number of labels, so that a higher sensitivity can be achieved (Wang and Merkoci, 2003, Langmuir 19:989; Zhao et al. 2003, J. Am. Chem. Soc. 125:11474). These methods do not provide the sensitivity required to detect quantities in the femtomole (fmol) range. Nor do they provide low non-specific binding, the ability to distinguish between complementary hybridization and a 2 base pair mismatch or multiple measurements.

The need remains, therefore, for highly sensitive detection systems (e.g., in the fmol range) that provide high selectivity and low non-specific binding. The system should have broad applicability so that it can be used to detect virtually any molecule of interest, provided it is capable of binding to or interacting with at least one other molecule (e.g., a specific binding partner). When the molecule of interest is a nucleic acid, e.g., DNA, the system should be able to distinguish between each of the following: complementary hybridization, at least 2-base pair-mismatched hybridization, and non-complementary DNA hybridization.

Ideally, the detection system will provide both a simple treatment to eliminate non-specific binding of the ECL label and high stability of the ECL label thereby allowing for the possibility of taking multiple measurements, without a loss of signal. Each of these needs, at least, is met by certain embodiments of those disclosed herein.

SUMMARY

The present application relates generally to methods and compositions for detecting analytes of interest in a sample. An analyte of interest can be associated with a disease or condition afflicting humans or other living organisms. Analytes of interest include toxins, chemical or biological warfare agents, and environmental pollutants. In certain embodiments the compositions may comprise a first and second carrier, an analyte of interest contained within a sample, an electrogenerated chemiluminescent (ECL) moiety entrapped or contained throughout the first carrier and at least one specific binding partner of the analyte of interest linked to at least one of the first and second carrier. Certain embodiments relate to methods of using these compositions to detect an analyte of interest in a sample.

In certain embodiments, methods and compositions for detecting an analyte of interest in a sample that is rapid, sensitive, and selective are provided. The application thus relates to methods and compositions for accurately detecting (e.g., with low occurrence of false positive signals) small quantities (e.g., 1 fmol) of analytes of interest that are contained within a sample. This desired sensitivity is achieved, at least in part, by providing a plurality of ECL molecules entrapped or contained within a first carrier.

In certain embodiments, the application provides a method of detecting an analyte of interest in a sample comprising: (a) forming a composition comprising:

$$(A)_{k}, (B)_{u}, (C), (D)_{x}$$

wherein A is an ECL moiety which can be induced to repeatedly emit electromagnetic radiation by direct exposure to an electrochemical energy source; B is a first carrier containing A and B is either linked to the analyte of interest or linked to a first specific binding partner of the analyte of interest; C is the sample which may contain the analyte of interest; and D is a second carrier which is either linked to the analyte of interest or linked to a second specific binding partner of the analyte of interest; wherein k, u, and x are each an integer equal to or greater than 1; (b) separating a complex comprising A, B, D, and the analyte of interest from other components of the composition; (c) inducing the ECL moiety to repeatedly emit electromagnetic radiation by exposing the moiety to electrochemical energy; and (d) detecting the emitted electromagnetic radiation and thereby detecting the presence of the analyte of interest, provided that B and D are not both linked to the analyte of interest.

In certain embodiments, the application provides a method of detecting a biological molecule of interest in a sample, comprising: (a) forming a composition comprising:

$(A)_k, (B)_u, (C), (D)_x$ wherein A is an ECL moiety which can be induced to repeatedly emit electromagnetic radiation by direct exposure to an electrochemical energy source; B is a first solid support encasing or containing A and B is either linked to the biological molecule of interest or linked to a first specific binding partner of the biological molecule of interest; C is the sample which may contain the biological molecule of interest; and D is a second solid support which is either linked to the biological molecule of interest or linked to a second specific binding partner of the biological molecule of interest; wherein k, u, and x are each an integer equal to or greater than 1; (b) separating a complex comprising A, B, D, and the biological molecule of interest from other components of the composition; (c) inducing the ECL moiety to repeatedly emit electromagnetic radiation by directly exposing the moiety to electrochemical energy; and (d) detecting the emitted electromagnetic radiation and thereby determining the presence of the biological molecule provided that B and D are not both linked to the biological molecule of interest.

In some embodiments, the biological molecule of interest can be a protein. In some embodiments, the biological molecule of interest can be a nucleic acid.

In certain embodiments, the application provides a composition useful for the detection of an analyte of interest in a sample, comprising:

$(A)_k, (B)_u, (C), (D)_x$ wherein A is an ECL moiety which can be induced to repeatedly emit electromagnetic radiation by direct exposure to an electrochemical energy source; B is a first carrier containing A and B is either linked to the analyte of interest or linked to a first specific binding partner of the analyte of interest; C is the sample which may contain the analyte of interest; and D is a second carrier which is either linked to the analyte of interest or linked to a second specific binding partner of the analyte of interest; wherein k, u, and x are each an integer equal to or greater than 1, provided that B and D are not both linked to the analyte of interest.

In certain embodiments, the application provides a composition useful for the detection of a biological molecule in a sample, comprising:

$(A)_k, (B)_u, (C), (D)_x$ wherein A is an ECL moiety which can be induced to repeatedly emit electromagnetic radiation by direct exposure to an electrochemical energy source; B is a first solid support containing A and B is either linked to the biological molecule of interest or linked to a specific binding partner of the biological molecule of interest; C is the sample which may contain the biological molecule; and D is a second solid support which can be directly linked to the biological molecule of interest or linked to a second specific binding partner of the biological molecule of interest; wherein k, u, and x are each an integer equal to or greater than 1, provided that B and D are not both linked to the biological molecule of interest.

In some embodiments, the biological molecule of interest can be a protein. In some embodiments, the biological molecule of interest can be a nucleic acid.

In certain embodiments, the application provides a method of detecting a nucleic acid molecule of interest in a sample, comprising: (a) forming a composition comprising:

$(A)_k, (B)_u, (C), (D)_x$ wherein A is an ECL moiety which can be induced to repeatedly emit electromagnetic radiation by direct exposure to an electrochemical energy source; B is a bead that is soluble in an organic solvent, for example, a polystyrene bead, containing A and B is either linked to the nucleic acid molecule of interest or linked to a first specific binding partner of the nucleic acid molecule of interest; C is the sample which may contain the nucleic acid molecule of interest; and D is a magnetic bead which is linked to the nucleic acid molecule of interest or linked to a second specific binding partner of the nucleic acid molecule of interest; wherein k, u, and x are each an integer equal to or greater than 1; (b) separating a complex comprising A, B, D, and the nucleic acid molecule of interest from other components of the composition; (c) dissolving B in an organic solvent; (d) inducing the ECL moiety to repeatedly emit electromagnetic radiation by directly exposing the moiety to electrochemical energy; and (e) detecting the emitted electromagnetic radiation and thereby detecting the presence of the nucleic acid molecule of interest, provided that B and D are not both linked to the nucleic acid molecule of interest.

In certain embodiments, the nucleic acid molecule of interest is a deoxyribonucleic acid (DNA). In some embodiments, the nucleic acid molecule of interest is a ribonucleic acid (RNA).

In certain embodiments, the application provides a composition useful for detecting a nucleic acid molecule of interest in a sample comprising:

$(A)_k, (B)_u, (C), (D)_x$ wherein A is a $Ru(bpy)_3[B(C_6F_5)_4]_2$ moiety, which can be induced to repeatedly emit electromagnetic radiation by direct exposure to an electrochemical energy source; B is a polystyrene bead containing A and B is either linked to the nucleic acid molecule of interest or linked to a binding partner of the nucleic acid molecule of interest; C is the sample which may contain the nucleic acid molecule of interest; and D is a magnetic bead which is either linked to the nucleic acid molecule of interest or linked to a specific binding partner of the nucleic acid molecule of interest; wherein k, u, and x are each an integer equal to or greater than 1, provided that B and D are not both linked to the nucleic acid molecule of interest.

In certain embodiments, the application provides a composition for detecting a nucleic acid molecule of interest in a sample comprising:

$(A)_k, (B)_u, (C), (D)_x$ wherein A is an ECL moiety which can be induced to repeatedly emit electromagnetic radiation by direct exposure to an electrochemical energy source; B is a polystyrene bead containing A and B is either linked to the nucleic acid molecule of interest or linked to a first specific binding partner of the nucleic acid molecule of interest; C is the sample which may contain the nucleic acid molecule of interest; and D is a magnetic bead which is linked to the nucleic acid molecule of interest or linked to a second specific binding partner of the nucleic acid molecule of interest; wherein k, u, and x are each an integer equal to or greater than 1, provided that B and D are not both linked to the nucleic acid molecule of interest.

In certain embodiments, the application provides a method of detecting a protein of interest in a sample, comprising: (a) forming a composition comprising:

$$(A)_k,(B)_u,(C),(D)_x$$

wherein A is an ECL moiety which can be induced to repeatedly emit electromagnetic radiation by direct exposure to an electrochemical energy source; B is a polystyrene bead containing A and B is linked either to the protein of interest or to a first specific binding partner which specifically binds to the protein of interest; C is the sample which may contain the protein of interest; D is a magnetic bead which can be linked to the protein of interest or to a second specific binding partner which specifically binds to the protein of interest; wherein k, u, and x are each an integer equal to or greater than 1; (b) separating a complex comprising A, B, D, and the protein molecule of interest from other components of the composition; (c) inducing the ECL moiety to repeatedly emit electromagnetic radiation by directly exposing the moiety to electrochemical energy; and (d) detecting the emitted electromagnetic radiation and thereby detecting the presence of the protein of interest, provided that B and D are not both linked to the protein of interest.

In certain embodiments, the first and/or the second binding partner of the protein of interest can be an antibody or a specific binding protein.

In certain embodiments, the application provides a composition for detecting a protein of interest in a sample comprising:

$$(A)_k,(B)_u,(C),(D)_x$$

wherein A is an ECL moiety which can be induced to repeatedly emit electromagnetic radiation by direct exposure to an electrochemical energy source; B is a polystyrene bead containing A and B is either linked to the protein of interest or linked to a first specific binding partner of the protein of interest; C is the sample which may contain the protein molecule of interest; and D is a magnetizable bead which is either linked to the protein of interest or linked to a second specific binding partner which specifically binds to the protein molecule of interest; and wherein k, u, and x are each an integer equal to or greater than 1, provided that B and D are not both linked to the protein of interest.

In certain embodiments, the first and/or the second binding partner of the protein molecule of interest can be an antibody or a specific binding protein.

The application also provides methods for performing competitive binding assays to detect an analyte of interest. In certain embodiments, the application provides a method of detecting an analyte of interest in a sample, comprising: (a) forming a composition comprising:

$$(A)_k,(B)_u,(C),(D)_x$$

wherein A is an ECL moiety which can be induced to repeatedly emit electromagnetic radiation by direct exposure to an electrochemical energy source; B is a first carrier containing A and B is either linked to an analog of the analyte of interest or linked to a specific binding partner of the analyte of interest; C is the sample which may contain the analyte of interest; and D is a second carrier which is either linked to an analog of the analyte of interest or linked to a specific binding partner of the analyte of interest; wherein k, u, and x are each an integer equal to or greater than 1; (b) separating a complex comprising A, B, D from other components of the composition; (c) inducing the ECL moiety in the complex to repeatedly emit electromagnetic radiation by directly exposing the moiety to electrochemical energy; and (d) detecting the emitted electromagnetic radiation and thereby detecting the presence of the analyte of interest, provided that only one of B and D is linked to the analog of the analyte of interest; and further provided that if B is linked to the analog of the analyte of interest, then D is linked to a binding partner of the analyte of interest and if B is linked to a binding partner of the analyte of interest, then D is linked to the analog of the analyte of interest.

In related embodiments, the application provides a method of detecting a nucleic acid molecule of interest in a sample comprising: (a) forming a composition comprising:

$$(A)_k,(B)_u,(C),(D)_x$$

wherein A is an ECL moiety which can be induced to repeatedly emit electromagnetic radiation by direct exposure to an electrochemical energy source; B is a polystyrene bead containing A and B is either linked to an analog of the nucleic acid of interest or linked to a specific binding partner of the nucleic acid molecule of interest; C is the sample which may contain the nucleic acid molecule of interest; and D is a magnetic bead which is either linked to an analog of the nucleic acid of interest or linked to a specific binding partner of the nucleic acid molecule of interest; wherein k, u, and x are each an integer equal to or greater than 1; (b) separating a complex comprising A, B, D, and the nucleic acid molecule of interest from other components of the composition; (c) dissolving B in an organic solvent; (d) inducing the ECL moiety to repeatedly emit electromagnetic radiation by directly exposing the moiety to electrochemical energy; and (e) detecting the emitted electromagnetic radiation and thereby detecting the presence of the nucleic acid molecule of interest, provided that only one of B and D is linked to the analog of the nucleic acid of interest; and further provided that if B is linked to the analog of the nucleic acid molecule of interest, then D is linked to a binding partner of the nucleic acid molecule of interest and if B is linked to a binding partner of the nucleic acid molecule of interest, then D is linked to the analog of the nucleic acid molecule of interest.

In some embodiments, the application provides, a method of detecting a protein of interest in a sample, comprising: (a) forming a composition comprising:

$$(A)_k,(B)_u,(C),(D)_x$$

wherein A is an ECL moiety which can be induced to repeatedly emit electromagnetic radiation by direct exposure to an electrochemical energy source; B is a polystyrene bead containing A and B is linked either to an analog of the protein of interest or to a specific binding partner which specifically binds to the protein of interest; C is the sample which may contain the protein of interest; D is a magnetic bead which is either linked to an analog of the protein of interest or to a specific binding partner which specifically binds to the protein of interest; wherein k, u, and x are each an integer equal to or greater than 1; (b) separating a complex comprising A, B, D, and the protein of interest from other components of the composition; (c) inducing the ECL moiety to repeatedly emit electromagnetic radiation by directly exposing the moiety to electrochemical energy; and (d) detecting the emitted electromagnetic radiation and thereby detecting the presence of the protein of interest; provided that only one of B and D is linked to the analog of the protein of interest; and further provided that if B is linked to the analog of the protein of interest, then D is linked to a specific binding partner of the protein of interest and if B is linked to a specific binding partner of the protein of interest, then D is linked to the analog of the protein of interest.

In some embodiments, the application provides compositions for performing competitive binding assays for the detection of analytes of interest. In some embodiments, the application provides a composition for detecting an analyte of interest in a sample comprising:

$$(A)_k, (B)_u, (C)_s, (D)_x$$

wherein A is an ECL moiety which can be induced to repeatedly emit electromagnetic radiation by direct exposure to an electrochemical energy source; B is a first carrier containing A and B is either linked to an analog of the analyte of interest or linked to a first specific binding partner of the analyte of interest; C is the sample which may contain the analyte of interest; D is a second carrier which can be linked to the analog of the analyte of interest or linked to a second specific binding partner of the analyte of interest; and wherein k, u, and x are each an integer equal to or greater than 1, provided that only one of B and D is linked to the analog of the analyte of interest and further provided that if B is linked to the analog of the analyte of interest, then D is linked to the specific binding partner of the protein of interest and if B is linked to the specific binding partner of the protein of interest, then D is linked to the analog of the protein of interest.

In certain embodiments of the composition the analyte of interest is a nucleic acid. In some embodiments of the composition, the analyte of interest is a protein.

In a related embodiment, the application provides a composition for detecting a nucleic acid molecule of interest in a sample comprising:

$$(A)_k, (B)_u, (C)_s, (D)_x$$

wherein A is an ECL moiety which can be induced to repeatedly emit electromagnetic radiation by direct exposure to an electrochemical energy source; B is a polystyrene bead containing A and B is either linked to an analog of the nucleic acid molecule of interest or linked to a specific binding partner of the nucleic acid molecule of interest; C is the sample which may contain the nucleic acid molecule of interest; D is a magnetic bead which is either linked to the analog of the nucleic acid molecule of interest or linked to the specific binding partner of the nucleic acid molecule of interest; and wherein k, u, and x are each an integer equal to or greater than 1, provided that only one of B and D is linked to the analog of the nucleic acid molecule of interest and further provided that if B is linked to the analog of the nucleic acid molecule of interest, then D is linked to the binding partner of the nucleic acid molecule of interest and if B is linked to the binding partner of the nucleic acid molecule of interest, then D is linked to the analog of the nucleic acid molecule of interest.

In certain embodiments, the nucleic acid molecule of interest is a deoxyribonucleic acid (DNA). In certain embodiments the nucleic acid molecule of interest is a ribonucleic acid (RNA).

In some embodiments, the application provides a composition for detecting a protein of interest in a sample comprising:

$$(A)_k, (B)_u, (C)_s, (D)_x$$

wherein A is an ECL moiety which can be induced to repeatedly emit electromagnetic radiation by direct exposure to an electrochemical energy source; B is a polystyrene bead containing A and B is either linked to an analog of the protein of interest or linked to a specific binding partner of the protein of interest; C is the sample which may contain the protein of interest; D is a magnetic bead which is either linked to the analog of the protein of interest or linked to the specific binding partner of the protein of interest; and wherein k, u, and x are each an integer equal to or greater than 1, provided that only one of B and D is linked to the analog of the protein of interest and further provided that if B is linked to the analog of the protein of interest, then D is linked to the binding partner of the protein of interest and if B is linked to the binding partner of the protein of interest, then D is linked to the analog of the protein of interest.

Additional embodiments provide kits useful for performing certain methods and forming certain compositions disclosed herein. In some embodiments, the application provides a kit for detecting an analyte of interest in a sample, comprising an ECL moiety which can be induced to repeatedly emit electromagnetic radiation by direct exposure to an electrochemical energy source; a first carrier containing the ECL moiety, wherein the first carrier is either linked to an analog of the analyte of interest or linked to a first specific binding partner of the analyte of interest; and a second carrier which is either linked to the analog of the analyte of interest or linked to a second specific binding partner of the analyte of interest.

A skilled artisan would understand that any of the embodiments, including methods, compositions and kits, described above, can also include more than one ECL moiety, provided each of the ECL moieties emits light at different wavelengths. Compositions, methods, and kits comprising two or more ECL moieties can be used, for example, to detect more than one analyte in a sample.

A skilled artisan would understand that any of the embodiments, including methods, compositions and kits, described above, can also include more than one ECL moiety, provided each of the ECL moieties emit light at different wavelengths. More than one ECL moiety is useful, for example, when more than one analyte can be detected.

It is to be understood that both the foregoing general description and the following detailed description are exemplary and explanatory only and are not restrictive of the methods and compositions, as described herein.

BRIEF DESCRIPTION OF THE DRAWINGS

FIG. 2A shows the beads after entrapping of $Ru(bpy)_3[B(C_6F_5)_4]_2$, and FIG. 2B shows the beads after covalent binding of avidin onto the surface of $Ru(bpy)_3[B(C_6F_5)_4]_2$ loaded beads. The exposure times used were 30 seconds. The specimens were excited at lamda$_{ex}$ 490 nm.

FIG. 6(e) shows the relative ECL intensities depicted in (a)-(d).

FIG. 8A shows that the DNA hybridization between probe DNA-MB (1.0 μm) and target DNA-Ru(II)<PSB/Avidin (10 μm) occurred at a ratio of MB/PSB=29. FIG. 8B shows that the DNA hybridization occurred between probe DNA-MB (2.8 μm) and target DNA-Ru(II)<PSB/Avidin (10 μm) at a ratio of MB/PSB=4.

FIG. 13B RUB loaded PSB; and FIG. 13C PSB only.

DESCRIPTION OF THE EMBODIMENTS

A. Definitions

Figure 1:
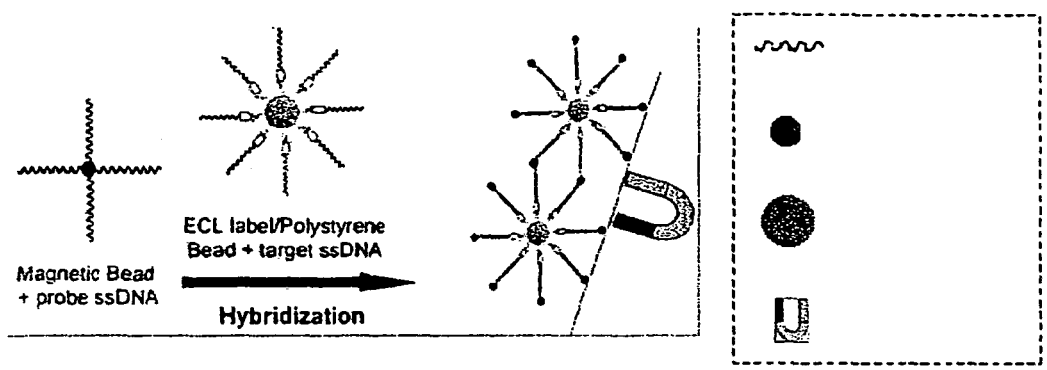
FIG. 1 shows a schematic diagram of a certain embodiment where the analyte of interest is a DNA molecule linked to a polystyrene bead which also serves as a first carrier containing an ECL label. Also shown is a second bead, which is magnetic and serves as a second carrier linked to a DNA molecule which is complementary to the DNA molecule linked to the polystyrene bead. The two DNA molecules bind to form a complex. Application of a magnetic field to the complex provides a means of isolating the analyte of interest (e.g., DNA) and detection of the ECL label provides a means of detection of the analyte of interest.

The term "antibody", as used herein, means an immunoglobulin or a part thereof, and encompasses any polypeptide comprising an antigen-binding site regardless of the source, method of production, or other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can bind antigen, for example, an Fab, F(ab')$_2$, Fv, scFv.

The term "analyte of interest", as used herein, means any molecule, or aggregate of molecules, including a cell or a cellular component of a virus, found in a sample. Also included are fragments of any molecule found in a sample. An analyte of interest can be an organic compound, an organometallic compound or an inorganic compound. An analyte of interest can be a nucleic acid (e.g., DNA, RNA, a plasmid, a vector, or an oligonucleotide), a protein (e.g., an antibody, an antigen, a receptor, a receptor ligand, or a peptide), a lipoprotein, a glycoprotein, a ribo- or deoxyribonucleoprotein, a peptide, a polysaccharide, a lipopolysaccharide, a lipid, a fatty acid, a vitamin, an amino acid, a pharmaceutical compound (e.g., tranquilizers, barbiturates, opiates, alcohols, tricyclic antidepressants, benzodiazepines, anti-virals, anti-fungals antibiotics, steroids, cardiac glycosides, or a metabolite of any of the preceding), a hormone, a growth factor, an enzyme, a coenzyme, an apoenzyme, haptens, lechtins, a substrate, a cellular metabolite, a cellular component or organelle (e.g., a membrane, a cell wall, a ribosome, a chromosome, a mitochondria, or a cytoskeleton component). Also included in the definition are toxins, pesticide, herbicides, and environmental pollutants. The definition further includes complexes comprising one or more of any of the examples set forth within this definition.

The term "analog of the analyte of interest", as used herein, means a substance that competes with the analyte of interest for binding to a specific binding partner. An analog of the analyte of interest can be a known amount of the analyte of interest itself that is added to compete for binding to a specific binding partner with analyte of interest present in a sample.

The term "carrier", as used herein, means one or more solid or liquid encapsulating substances. A carrier can comprise organic or inorganic compounds and it can be used for at least one of the following: to present a sample, to present a specific binding partner, or to contain or entrap an ECL moiety. Carriers are described in further detail infra.

The terms "containing" or "contained", as used herein, refer to the non-specific association between the interior of a carrier and an ECL moiety, such that the ECL moiety and the carrier are in physical contact with one another, but are not necessarily attached to each other. In certain embodiments, an ECL moiety contained within a carrier can be linked to the carrier. In certain embodiments the ECL moiety contained within a carrier is not linked to the carrier. The terms containing/contained are used interchangeably with the terms "encased/encasing," and "entrapped/entrapping."

The term "hybridizing", as used herein, refers to the formation of duplexes between one nucleotide sequence and a second nucleotide sequence under appropriate conditions. In some embodiments the appropriate conditions can be stringent conditions. Stringent conditions are sequence-dependent and will be different in different circumstances. Longer sequences hybridize specifically at higher temperatures (see, e.g., Sambrook et al. 1989, Molecular Cloning A Laboratory Manual, Cold Spring Harbor Laboratory, N.Y. and Ausubel et al. 1989, Current Protocols in Molecular Biology, Greene Publishing Associates and Wiley Interscience, N.Y.). Generally, stringent conditions are selected to be about 5° C., lower than the thermal melting point ($T_m$) for the specific sequence at a defined ionic strength and pH. The $T_m$ is the temperature (under defined ionic strength, pH, and nucleic acid concentration) at which 50% of the polynucleotides complementary to the target sequence hybridize to the target sequence at equilibrium. Typically, stringent conditions will be those in which the salt concentration is less than about 1.0 M sodium ion, typically about 0.05 to 1.0 M sodium ion concentration (or other salts) at pH 7.0 to 8.3 and the temperature is at least about 30° C. for short probes (e.g.,10 to 50 nucleotides) and at least about 60° C. for long probes (e.g., greater than 50 nucleotides). Stringent conditions can also be achieved with the addition of destabilizing agents such as formamide. Each increase of 1% in the formamide concentration of a solution lowers the $T_m$ of a DNA duplex by about 0.7° C.

Hybridization can occur between polynucleotides that are 100% complementary, i.e., when there are no mismatches between the two strands of a double-stranded nucleic acid. Hybridization can also occur when there are mismatches between the two strands of a double-stranded nucleic acid. Complementary hybridization, as used herein, refers to the hybridization between two strands of nucleic acid where there is no more than one mismatch between the two hybridized strands of a double-stranded nucleic acid.

The term "linked" as used herein encompasses both direct covalent connections between two moieties, direct noncovalent connections between two moieties, and indirect connections between two moieties that are mediated by one or more additional moieties. For example, a direct covalent connection between two moieties can include an amide bond between two amino acids, a direct noncovalent connections between two moieties can include an ionic interaction between a metal and a base to form a salt, or a hydrogen bond between two water molecules. Indirect connections between two moieties that are mediated by one or more additional moieties can include a fusion protein, such as an Ig fusion protein and a receptor, such as a TNF receptor, where the bond between the Ig and the TNF receptor is mediated by a linker, such as short amino acid sequence that is not native to either the Ig or TNF receptor.

The term "linked" does not encompass connections that are mediated by an analyte of interest.

The term "magnetizable" as used herein refers to a property of matter wherein the permeability of the matter differs from that of free space. The term includes paramagnetizable and superparamagnetizable.

The term "nucleic acid," as used herein, refers to polymers comprised of deoxyribonucleotides or ribonucleotides in either single- or double-stranded form. Typically a single-stranded nucleic acid will comprise more than 100 bases and a double-stranded nucleic acid will comprise more than 100 base pairs. The term "nucleic acid" encompasses nucleic acids containing naturally occurring nucleotides as well as analogues of natural nucleotides that have binding properties similar to the reference nucleic acid. The term nucleic acid also includes cDNA or an mRNA encoded by a gene. A nucleic acid will be able to hybridize to its complement through complementary base pairing, e.g., via a hydrogen bond.

The term "oligonucleotide," as used herein, refers to a single-stranded nucleic acid that typically is less than or equal to 100 bases long. Of course, complementary oligonucleotides can be annealed to form a double-stranded polynucleotide. As used herein, an oligonucleotide can include natural (i.e., A, G, C, T, or U) or modified bases. In addition, the bases in an oligonucleotide can be joined by a linkage other than a phosphodiester bond, so long as it does not interfere with interstrand base pairing. Thus, for example, oligonucleotides can be peptide-nucleic acids in which the constituent bases are joined by peptide bonds rather than phosphodiester linkages. (see e.g. Nielson, 2001, Current Opinion in Biotechnology 12:16). It will be understood by one of skill in the art that oligonucleotides can hybridize with sequences lacking complete complementarity with the probe sequence and the methods described herein can be used to distinguish between binding that is completely complementary and that which is less than completely complementary. Optionally, the oligonucleotides can be directly labeled with radioisotopes, chromophores, lumiphores, chromogens, or ECL moieties or can be indirectly labeled, for example, with biotin to which a streptavidin or avidin complex can later bind.

The term "polynucleotide," as used herein, refers to a polymer comprised of more than 2 nucleotides, and less than 100 nucleotides.

The term "sample," as used herein, means any specimen derived from, or originating in, a biological system. Biological systems include ecological systems (e.g., a water, air or soil specimen) or, organisms (e.g., a plant, an animal, fungi, bacteria, other eukaryotes or prokaryotes), or viruses or prions. The sample can contain an analyte of interest. The term sample can also include an isolated, e.g., purified analyte of interest.

The term "specific binding partner," as used herein, refers to a first molecule that can form a relatively stable complex with a second molecule under physiologic conditions. In general, specific binding is characterized by a relatively high affinity and a relatively low to moderate capacity. Nonspecific binding usually has a low affinity with a moderate to high capacity. Typically, binding is considered specific when the affinity constant $K_a$ is higher than about $10^6$ $M^{-1}$, or is higher than about $10^8$ $M^{-1}$. A higher affinity constant indicates greater affinity, and thus greater specificity. Antibodies typically bind antigens with an affinity constant in the range of $10^6$ $M^{-1}$ to $10^9$ $M^{-1}$ or higher. If desired, nonspecific binding can be reduced without substantially affecting specific binding by varying the binding conditions. Such conditions are known in the art, and a skilled artisan using routine techniques can select appropriate conditions. The conditions can be defined, for example, in terms of molecular concentration, ionic strength of the solution, temperature, time allowed for binding, concentration of unrelated molecules (e.g., serum albumin, milk casein), etc.

Examples of specific binding partners include complementary nucleic acid sequences (e.g., two DNA sequences which hybridize to each other; two RNA sequences which hybridize to each other; or a DNA and an RNA sequence which hybridize to each other), an antibody and an antigen, a receptor and a ligand (e.g., TNF and TNFr-I, CD142 and Factor VIIa, B7-2 and CD28, HIV-1 and CD4, ATR/TEM8 or CMG and the protective antigen moiety of anthrax toxin), an enzyme and a substrate, or a molecule and a binding protein (e.g., vitamin B12 and intrinsic factor, folate and folate binding protein). A specific binding partner can also be an analog of a naturally occurring specific binding partner. Examples of analogs include azidothymidine (AZT), an analog of a nucleotide which binds to HIV reverse transcriptase, puromycin, an analog of the terminal amino-acyl-adenosine part of aminoacyl-tRNA, and methotrexate, an analog of tetrahydrofolate. Other analogs can be derivatives of the analyte of interest.

B. Electrogenerated Chemiluminescent Substances

In certain embodiments, the application provides for detecting an analyte of interest in a sample using ECL. The ECL moiety can be any compound that can be induced to repeatedly emit electromagnetic radiation by direct exposure to an electrochemical energy source. In some embodiments, the ECL moiety can be induced to repeatedly emit electromagnetic radiation in the presence of a coreactant. In some embodiments, the ECL moiety can comprise a metal-containing organic compound wherein the metal is chosen, for example, from ruthenium, osmium, rhenium, iridium, rhodium, platinum, palladium, molybdenum, and technetium. In some embodiments, the metal is ruthenium or osmium. The metal can also be chosen, for example, from rare earth metals, including but not limited to, cerium, dysprosium, erbium, europium, gadolinium, holmium, lanthanum, lutetium, neodymium, praseodymium, promethium, terbium, thulium, and ytterbium. In some embodiments, the metal is cerium, europium, terbium, or ytterbium.

According to certain embodiments, a metal-containing ECL moiety as employed herein may have the formula $BF_4$ $$M(P)_m(L^1)_n(L^2)_o(L^3)_p(L^4)_q(L^5)_r(L^6)_s$$

wherein M is a metal; P is a polydentate ligand of M; $L^1$, $L^2$, $L^3$, $L^4$, $L^5$ and $L^6$ are ligands of M, each of which can be the same as, or different from, each other ligand; m is an integer equal to or greater than 1; each of n, o, p, q, r and s is an integer equal to or greater than zero; and P, $L^1$, $L^2$, $L^3$, $L^4$, $L^5$ and $L^6$ are of such composition and number that the ECL moiety can be induced to emit electromagnetic radiation and the total number of bonds to M provided by the ligands of M equals the coordination number of M.

In some embodiments, M is ruthenium. In some embodiments, M is osmium.

In certain embodiments, the ECL moiety has one polydentate ligand of M. In some embodiments, the ECL moiety has more than one polydentate ligand. In embodiments comprising more than one polydentate ligand of M, the polydentate ligands can be the same or different. Polydentate ligands include aromatic and aliphatic ligands. Suitable aromatic polydentate ligands include aromatic heterocyclic ligands and can be nitrogen-containing, such as, for example, bipyridyl, bipyrazyl, terpyridyl, 1,10 phenanthroline, and porphyrins.

Suitable polydentate ligands can be unsubstituted, or substituted by any of a large number of substituents known to the art. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide sulfur-containing groups, phosphorus containing groups, and the carboxylate ester of N-hydroxysuccinimide.

Additionally, at least one of $L^1$, $L^2$, $L^3$, $L^4$, $L^5$ and $L^6$ can be a polydentate aromatic heterocyclic ligand. Furthermore, at least one of these polydentate aromatic heterocyclic ligands can contain nitrogen. Suitable polydentate ligands include, but are not limited to, bipyridyl, bipyrazyl, terpyridyl, 1,10 phenanthroline, a porphyrin, substituted bipyridyl, substituted bipyrazyl, substituted terpyridyl, substituted 1,10 phenanthroline or a substituted porphyrin. These substituted polydentate ligands can be substituted with an alkyl, substituted alkyl, aryl, substituted aryl, aralkyl, substituted aralkyl, carboxylate, carboxaldehyde, carboxamide, cyano, amino, hydroxy, imino, hydroxycarbonyl, aminoarbonyl, amidine, guanidinium, ureide, maleimide a sulfur-containing group, a phosphorus-containing group or the carboxylate ester of N-hydroxysuccinimide.

In some embodiments, the ECL moiety can contain two bidentate ligands, each of which can be bipyridyl, bipyrazyl, terpyridyl, 1,10 phenanthroline, substituted bipyridyl, substituted bipyrazyl, substituted terpyridyl or substituted 1,10 phenanthroline.

In certain embodiments, the ECL moiety can contain three bidentate ligands, each of which can be bipyridyl, bipyrazyl, terpyridyl, 1,10 phenanthroline, substituted bipyridyl, substituted bipyrazyl, substituted terpyridyl or substituted 1,10 phenanthroline. The ECL moiety can comprise ruthenium. In some embodiments, the ECL moiety can comprise ruthenium, two bidentate bipyridyl ligands, and one substituted bidentate bipyridyl ligand.

In some embodiments, the ECL moiety can contain a tetradentate ligand such as a porphyrin or substituted porphyrin.

The ECL moiety can have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stibines, and arsines.

Certain embodiments of this ECL moiety comprise bis(2,2'-bipyridyl)ruthenium(II) and tris(2,2'-bipyridyl)ruthenium (II).

One or more of the ligands of M may be attached to additional chemical labels, such as, for example, radioactive isotopes, fluorescent components, or additional luminescent ruthenium- or osmium-containing centers.

In some embodiments, the ECL moiety is tris(2,2'-bipyridyl)ruthenium(II) tetrakis(pentafluorophenyl)borate. In some embodiments, the ECL moiety is bis[(4,4'-carbomethoxy)-2,2'-bipyridine]2-[3-(4-methyl-2,2'-bipyridine-4-yl)propyl]-1,3-dioxolane ruthenium (II). In some embodiments, the ECL moiety is bis(2,2'bipyridine)[4-(butan-1-a1)-4'-methyl-2,2'-bipyridine]ruthenium (II). In a further embodiment, the ECL moiety is bis(2,2'-bipyridine)[4-(4'-methyl-2,2'-bipyridine-4'-yl)-butyric acid]ruthenium (II). In some embodiments, the ECL moiety is (2,2'-bipyridine)[cis-bis(1,2-diphenylphosphino)ethylenel]{2-[3-(4-met-hyl-2,2'-bipyridine-4'-yl)propyl]-1,3-dioxolane}osmium (II). In yet a further embodiment, the ECL moiety is bis(2,2'-bipyridine)[4-(4'-methyl-2,2'-bipyridine)-butylamine]ruthenium (II). In some embodiments, the ECL moiety is bis(2,2'-bipyridine)[1-bromo-4(4'-methyl-2,2'-bipyridine-4-yl)butane]ruthenium (II). In still a further embodiment, the ECL moiety is bis(2,2'-bipyridine)maleimidohexanoic acid, 4-methyl-2,2'-bipyridine-4'-butylamide ruthenium (II).

In some embodiments, the ECL moiety does not comprise a metal and can be, for example, rubrene or 9,10-diphenylanthracene.

In some embodiments, the ECL moiety can be contained or encased in a carrier. The number of ECL molecules encased in or adsorbed to the carrier will depend on the size of the ECL molecule and the size of the carrier. The carrier can contain $1\times10^2$-$1\times10^{20}$, $1\times10^2$-$1\times10^{15}$, $1\times10^4$-$1\times10^{12}$, $1\times10^2$-$1\times10^{10}$, $1\times10^6$-$1\times10^{10}$, or $1\times10^6$-$1\times10^9$ ECL molecules. In some embodiments, the ECL moiety can be contained or encased in a carrier and linked to the surface of the carrier, e.g., by a covalent bond or a non-covalent interaction.

The term "ECL coreactant," as used herein, herein, pertains to a chemical compound that either by itself or via its electrochemical reduction oxidation product(s), plays a role in the ECL reaction sequence.

Often ECL coreactants can permit the use of simpler means for generating ECL (e.g., the use of only half of the double-step oxidation-reduction cycle) and/or improved ECL intensity. In some embodiments, coreactants can be chemical compounds which, upon electrochemical oxidation/reduction, yield, either directly or upon further reaction, strong oxidizing or reducing species in solution. A coreactant can be peroxodisulfate (i.e., $S_2O_8^{2-}$, persulfate) which is irreversibly electro-reduced to form oxidizing $SO_4^-$ ions. The coreactant can also be oxalate (i.e., $C_2O_4^{2-}$) which is irreversibly electro-oxidized to form reducing $CO_2^-$ ions. A class of coreactants that can act as reducing agents is amines or compounds containing amine groups, including, for example, tri-n-propylamine (i.e., $N(CH_2CH_2CH_3)_3$, TPrA). In some embodiments, tertiary amines can be better coreactants than secondary amines. In some embodiments, secondary amines can be better coreactants than primary amines.

Coreactants include, but are not limited to, lincomycin; clindamycin-2-phosphate; erythromycin; 1-methylpyrrolidone; diphenidol; atropine; trazodone; hydroflumethiazide; hydrochlorothiazide; clindamycin; tetracycline; streptomycin; gentamicin; reserpine; trimethylamine; tri-n-butylphosphine; piperidine; N,N-dimethylaniline; pheniramine; bromopheniramine; chloropheniramine; diphenylhydramine; 2-dimethylaminopyridine; pyrilamine; 2-benzylaminopyridine; leucine; valine; glutamic acid; phenylalanine; alanine; arginine; histidine; cysteine; tryptophan; tyrosine; hydroxyproline; asparagine; methionine; threonine; serine; cyclothiazide; trichlormethiazide; 1,3-diaminopropane; piperazine, chlorothiazide; hydrazinothalazine; barbituric acid; persulfate; penicillin; 1-piperidinyl ethanol; 1,4-diaminobutane; 1,5-diaminopentane; 1,6-diaminohexane; ethylenediamine; benzenesulfonamide; tetramethylsulfone; ethylamine; di-ethylamine; tri-ethylamine; tri-iso-propylamine; di-n-propylamine; di-iso-propylamine; di-n-butylamine; tri-n-butylamine; tri-iso-butylamine; bi-iso-butylamine; s-butylamine; t-butylamine; di-n-pentylamine; tri-n-pentylamine; n-hexylamine; hydrazine sulfate; glucose; n-methylacetamide; phosphonoacetic acid; and/or salts thereof.

Coreactants also include, but are not limited to, N-ethylmorpholine; sparteine; tri-n-butylamine; piperazine-1,4-bis (2-ethanesulfonic acid) (PIPES); triethanolamine; dihydronicotinamide adenine dinucleotide; 1,4-diazobicyclo (2.2.2)octane; ethylenediamine tetraacetic acid; oxalic acid; 1-ethylpiperidine; di-n-propylamine; N,N,N',N'-Tetrapropyl-1,3-diaminopropane; DAB-AM-4, Polypropylenimine tetraamine Dendrimer; DAB-AM-8, Polypropylenimine octaamine Dendrimer; DAB-AM-16, Polypropylenimine hexadecaamine Dendrimer; DAB-AM-32, Polypropylenimine dotriacontaamine Dendrimer; DAB-AM-64, Polypropylenimine tetrahexacontaamine Dendrimer; 3-(N-Morpholino)propanesulfonic acid; 3-Morpholino-2-hydroxypropanesulfonic acid; Glycyl-glycine; 2-Morpholinoethanesulfonic acid; 2,2-Bis(hydroxymethyl)-2,2',2''-nitrilotriethanol; N-(2-Acetamido) iminodiacetic acid; N,N-Bis(2-hydroxyethyl)taurine; N-(2-Hydroxyethyl) piperazine-N'-(2-ethanesulfonic acid); N,N-Bis(2-hydroxyethyl)-3-amino-2-hydroxypropanesulfonic acid; 4-(N-Morpholino)butanesulfonic acid; 4-(2-Hydroxyethyl)piperazine-1-(2-hydroxypropanesulfonic acid) Hydrate; Piperazine-1, 4-bis(2-hydroxypropanesulfonic acid) dihydrate; 4-(2-Hydroxyethyl)piperazine-1-propanesulfonic acid; N,N-Bis (2-hydroxyethyl)glycine; N-(2-Hydroxyethyl)piperazine-N'-(4-butanesulfonic acid); and/or salts thereof.

ECL measurements according to the present methods can be made in organic solvents such as acetonitrile, in partially aqueous systems, or in aqueous systems. A suitable electrode for the electrochemical reduction of an ECL moiety can be, for example, a Pt electrode or an electrode comprised of an alloy of Pt and Ir.

C. Carriers

In certain embodiments, the application provides for a first and second carrier which can be used in the detection of an analyte of interest. The first and second carriers can serve at least one of several functions, including presentation of a sample, presentation of a specific binding partner, containment or entrapment of an ECL moiety, and providing a means for separating a complex formed between an analyte of interest and a specific binding partner from other components of the composition.

Either the first or second carrier can comprise an ECL moiety. In certain embodiments, the ECL moiety can be contained in the carrier. Because the ECL moiety is contained within a carrier, the application provides for readily releasing the ECL moiety from the carrier, e.g., by changing certain conditions such as the nature of the solvent. In certain embodiments, e.g., where the carrier is a solid support comprised of a material such as plastic, the ECL moiety is not blended into the carrier. In some embodiments, the ECL moiety can be covalently linked to the surface of the carrier and contained within the carrier. In some embodiments, the ECL moiety can be contained within the carrier and adsorbed to the surface of the carrier. The first carrier can optionally be comprised of the sample containing the analyte of interest. In certain embodiments, the sample can be linked to the surface of the first carrier, thus making it available for binding with a specific binding partner. In certain embodiments, however, the sample can be linked to neither the first or second carrier. In this embodiment, the sample can be in solution.

In certain embodiments, either the first carrier or second carrier can comprise a specific binding partner of the analyte of interest. The specific binding partner can be linked to the surface of the first carrier thereby making it accessible for binding to the analyte of interest.

In embodiments comprising a second carrier, the second carrier can comprise a specific binding partner of the analyte of interest. The specific binding partner can be linked to the surface of the second carrier thereby making it accessible for binding to the analyte of interest. The second carrier can comprise a means for separating a complex formed between the analyte of interest and the specific binding partner. In certain embodiments, the second carrier can provide a means of separating the complex formed between the analyte of interest and the specific binding partner from other components of the composition. For example, the second carrier can be magnetizable allowing the complex formed between the analyte of interest and the specific binding partner to be separated from other components of the composition using a magnet. In certain embodiments, the magnet used to separate the complex from other components of the composition can be located proximal to an electrode that can be used to introduce electrochemical energy into the system as described, for example, in U.S. Pat. Nos. 5,935,779 and 6,325,973.

In certain embodiments, at least one of the first and second carriers can be a solid support. In some embodiments both the first and second carriers are solid supports. The solid support can comprise a particle, i.e., a polymer having a length greater than 1000 micrometers in at least one dimension, a nanoparticle, i.e., a polymer having a length in the range of 1-1000 nanometers in at least one dimension, or a microparticle, i.e., a polymer having a length greater than 1000 nanometers, but less than or equal to 1000 micrometers in at least one dimension. In certain embodiments the solid support can have a three dimensional shape including both irregular and regular shapes, e.g. spherical, cubic, conical.

The solid supports can comprise a bead, a gel, or a membrane. A membrane can comprise, for example, nitrocellulose, nylon, polyvinylidene fluoride (PVDF) or carboxylated polyvinylidene (U.S. Pat. No. 6,037,124). The membrane can be coated with polyvinyl benzyl dimethyl hydroxyethyl ammonium chloride, polyvinyl benzyl benzoyl aminoethyl dimethyl ammonium chloride, polyvinyl benzyl tributyl ammonium chloride, copolymers of polyvinyl benzyl trihexyl ammonium chloride and polyvinyl benzyl tributyl ammonium chloride, copolymers of polyvinyl benzyl benzyl dimethyl ammonium chloride and polyvinyl aminoethyl dimethyl ammonium chloride and copolymers of polyvinyl benzyl phenyl ureidoethyl dimethyl ammonium chloride and polyvinyl benzyl benzyl dimethyl ammonium chloride (U.S. Pat. No. 5,336,596). The solid support can comprise any material which can be linked to a specific binding partner of the analyte of interest and/or the sample (e.g. polystyrene, sepharose, sephadex) and/or which can contain or entrap an ECL moiety. Solid supports can comprise any synthetic organic polymer such as polyacrylic, vinyl polymers, acrylate, polymethacrylate, polyacrylamide, polyacylonitriles, and polyolefins. Solid supports can also comprise a carbohydrate polymer, e.g., agarose, cellulose, hyaluronic acid, chitin, acyl gellan, dextran, carboxymethylcellulose, carboxymethyl starch, carboxymethyl chitin, poly(lactide-co-ethylene glycol). Solid supports can comprise inorganic oxides, such as silica, zirconia, e.g., carbon clad zirconia (U.S. Pat. No. 5,182,016), titania, ceria, alumina, manganese, magnesia (i.e., magnesium oxide), calcium oxide, controlled pore glass (CPG). Solid supports can also comprise combinations of some of the above-mentioned supports including, but not limited to, dextran-acrylamide. A solid support can be prepared to minimize non-specific interactions with the specific binding partner and/or the analyte of interest.

In certain embodiments where at least one of the first or second carriers is a solid support, the solid support can be insoluble in an aqueous environment, but soluble in an organic environment, e.g., acetonitrile, ether, chloroform, benzene. For embodiments in which an ECL moiety is entrapped or otherwise associated with such a solid support, the ECL moiety can be released by placing the solid support in an organic environment, thereby facilitating detection of the ECL moiety. An organic environment can include a solvent that is 70-100%, 80-100%, 90-99%, 99-99.99% organic solvent (volume/volume).

In some embodiments, at least one of the first or second carriers is a gel having a melting point in the range of 30° C.-60° C., e.g., low melting temperature agarose. In these embodiments, heating the complex above the melting point of the carrier containing the ECL moiety will release the ECL moiety and thereby facilitate detection.

In certain embodiments, the solid support is a bead, e.g., a polystyrene bead. In embodiments where both the first and second carriers are beads, the first carrier can have an ECL moiety contained or entrapped within it, and the second carrier can be a magnetizable bead. Both the ECL-containing bead and the magnetizable bead can have a diameter in the range of 0.1 µm-100 µm, 0.5 µm-50 µm, 1 µm-20 µm, or 0.5 µm-10 µm. In some embodiments, the first carrier can have a diameter of 10 µm and the second carrier can have a diameter of 1 µm. In some embodiments, the first carrier can have a diameter of 10 µm and the second carrier can have a diameter of 2.8 µm.

In certain embodiments, at least one of the carriers can comprise a liquid. The liquid can comprise at least one amphiphilic molecule. An amphiphilic molecule is one having both polar and non-polar portions and which can form aggregates, e.g. micelles, in an aqueous environment. Thus a micelle can be comprised of any fatty acid ion such as palmitate or oleate. A micelle can comprise one or more non-ionic detergents, e.g., Triton X-100, or Octyl-.beta.-D-glucoside. A micelle can comprise one or more ionic detergents, e.g., sodium dodecyl sulfate, deoxycholate, lysolecithin. In some embodiments, a micelle can comprise both ionic and nonionic detergents.

Thus in certain embodiments, at least one of the first and second carriers can be a micelle. The micelle can be linked to the sample, so that the analyte of interest is exposed on the surface of the micelle, thus allowing the specific binding partner to contact the analyte of interest. The ECL moiety can be contained within the interior of the micelle. Disruption of the micelle, e.g. through agitation or sonication, or oxidation or reduction, will thus provide a means of releasing the ECL and facilitate detection of the analyte of interest.

In certain embodiments, the carrier can be a liposome. Liposomes are microscopic spherical vesicles that form when phospholipids are hydrated. When mixed in water under low shear conditions, the phospholipids arrange themselves in sheets, the molecules aligning side by side in like orientation, "heads" up and "tails" down. These sheets then join tails-to-tails to form a bilayer membrane in a phospholipid sphere with an aqueous center. Liposomes can be of uniform size, e.g., 200 nm in diameter. Liposomes enable water soluble and water insoluble materials to be used together in a formulation without the use of surfactants or other emulsifiers. Water soluble materials are dissolved in the water in which the phospholipids are hydrated, and when the liposomes form these materials are trapped in the aqueous center. The liposome wall, being a phospholipid membrane, holds fat soluble materials such as oils. Liposomes can be comprised of stabilized natural phospholipid mixtures, synthetic identical-chain phospholipids, glycolipid-containing liposomes, bipolar fatty acids, methyvmethylene x-linked, lipoprotein-coated, or carbohydrate-coated. The sample can be presented on the surface of the liposome to facilitate binding of the specific binding partner or the sample. The liposome can contain within it (i.e., in the aqueous center or in the surrounding lipid) an ECL moiety, see, e.g., U.S. Pat. No. 6,706,861.

D. Methods of Linking a Sample or Specific Binding Partner to a Carrier

The sample containing the analyte of interest or the specific binding partner can be linked to a carrier by any means known in the art. For example, crosslinking reagents can be used for proteins and nucleic acids (Lund et al. 1988, Nucleic Acids Res. 16:10861). Similarly, photoreactive crosslinking reagents have been used for both nucleic acids and proteins (Penchovsky et al. 2000, Nucleic Acids Res.

28(22):98; Harrison et al. 1989, Biochemistry 28:6023). Selection of the appropriate means will depend on the nature of the sample and the nature of the carrier. The linkage can be, for example, by a covalent bond, a non-covalent interaction such as an electrostatic interaction, a hydrophobic interaction, a hydrophilic interaction, a van der Waals interaction, or a hydrogen bond. Selecting a method of linking a sample to a carrier is well within the ordinary skill in the art.

In certain embodiments, ligands are immobilized or "linked" directly to a carrier by forming covalent chemical bonds between particular functional groups on the ligand (e.g., primary amines, sulfhydryls, carboxylic acids, aldehydes) and reactive groups on the carrier.

Other linking approaches are also possible, including but not limited to using biotin with avidin or streptavidin as a linker. Methods of using biotin/avidin streptavidin as linkers are known in the art (see, Wilchek and Bayer, Eds. Methods in Enzymology vol. 184, Academic Press, San Diego 1990). In certain embodiments, N-hydroxysuccinimide (NHS) can be used to form an NHS ester of biotin. The biotin residue can be linked to a variety of functional groups including but not limited to primary amines on lysine residues, carboxyl moieties on glutamate or aspartate residues, or sulfhydryl moieties on cysteine residues. Avidin can be covalently linked to a carrier via an amino group on lysine after activation of the carrier with cyanogen bromide (CNBr).

In certain embodiments, the sample or the binding partner can be simply adsorbed on the surface of the carrier. For example, antibodies can be adsorbed to the surface of polystyrene microspheres. For maximum surface coverage (up to a monolayer) in embodiments in which it is desired to adsorb a protein to the surface of a carrier, the pH of the solution can be adjusted to, or slightly more basic than, the protein's isoelectric point. Using a dilute microsphere suspension (about 1% solids) ensures coating of single microspheres. While a final protein concentration of about 0.1 mg/ml is usually enough to achieve a monolayer of protein, adding about 3 to about 10 times that amount ensures favorable stoichiometry and a good driving force for binding.

The surface of a carrier can be modified to facilitate the covalent linkage of the sample or the specific binding partner. Surface-modified polymeric microspheres are often made by copolymerizing styrene with a small amount (less than about 5%) of a functional monomer, such as acrylic acid, which yields microspheres covered with —COOH groups. Other monomers can be used to prepare microspheres with different surface chemistries, see, e.g., U.S. Pat. No. 5,599,889.

Native silanol groups on the surface of silica microspheres can be reacted with aqueous or solvent-based silane linking agents to yield preactivated silica microspheres with a large variety of surface functional groups. Examples include chloromethyl, carboxyl, and amino groups. DNA and RNA can be adsorbed onto silica in the presence of chaotropic agents. Oligonucleotides can be covalently bound to surface-modified silica via the 5'-amino end. Lipids can be bound via the carboxyl group on the fatty acid chain and propylamine surface groups on the silica as described by Boom et al., 1990, J. Clin. Microbiol., 28:495).

An analyte of interest or a specific binding partner can be incorporated into a micelle, see, e.g., Savic et al., 2003, Science 300:615; Maysinger et al., 2001, Biochim. Biophys. Acta. 1539(3):205. Solubilization and reconstitution of a protein into detergent micelles can be performed, for example, by slowly diluting the protein solution in 6 M guanidine hydrochloride (Gdn.HCl) into an excess of refolding buffer (e.g., 3% dihexanoyl phosphatidylcholine 20 mM Tris.HCl/5 mM EDTA/0.6 M L-arginine, pH 8.5). After removing the residual Gdn-HCl, for example, by dialysis, the solution can be concentrated by a variety of techniques, including ultrafiltration. See, e.g., Fernandez et al. 2001, Proc. Natl. Acad. Sci. USA 98:2358.

An analyte of interest, or a specific binding partner can be incorporated into a liposome. Many methods of incorporating proteins into liposomes are known (see, e.g., Rigaud., et al., "Liposomes as Tools for the Reconstitution of Biological Systems," p. 71-88, in Liposomes as Tools in Basic Research and Industry, ed. Philippot, J. R. and Schuber, CRC Press, Boca Raton, Fla. (1995)). As an example, mechanical means, such as a sonicator or French press, can be used to produce unilamellar vesicles by swelling and drying phospholipids films in excess buffer (Lelkes et al., 1985, J. Biol. Chem. 260:1796). Alternatively, proteins can be spontaneously incorporated into preformed liposomes catalyzed by low cholate or lysolecithin concentrations (Wrigglesworth et al., 1987, Biochem J. 246(3):737). Proteins can also be co-solubilized in the presence of phospholipids and detergent, to form micelles followed by the subsequent removal of the detergent. Large liposomes can be prepared by reverse-phase evaporation and treated with various amounts of the detergents such as Triton X-100, octyl glucoside, or sodium cholate. At each step of the solubilization process, protein can be added. The protein-phospholipid detergent mixtures can then be subjected to SM2 Bio-Beads treatments to remove the detergent (Rigaud et al., 1988, Biochemistry 27(8):2677). Membrane proteins can be incorporated into liposomes by providing the membrane protein in solution; providing a solution of preformed liposomes; and incubating the mixture. Prior to the step of providing a solution of preformed liposomes, the liposomes are formed by combining a mixture of phospholipids with a solution of at least one type of unsaturated fatty acid (U.S. Pat. No. 6,706,861). The skilled artisan will recognize that there are many additional ways to link the sample to a carrier.

E. Methods of Loading an ECL Moiety Into a Carrier

In certain embodiments, the ECL moiety can be linked to the surface of a carrier. Methods described above regarding linking a sample to a carrier can be similarly used to link an ECL moiety to a carrier. Where the carrier is a solid support, e.g., a bead, the ECL moiety can be linked to the surface of the carrier, for example, via a covalent bond, a non-covalent interaction, an electrostatic interaction, a hydrophobic interaction, a hydrophilic interaction, a van der Waals interaction, or a hydrogen bond.

In some embodiments, the ECL moiety is soluble in organic solvents, but insoluble in aqueous solvents. The ECL moiety can be dissolved in an organic solvent and then mixed with a plurality of carrier particles, e.g., a bead comprised of a hydrophobic material such as polystyrene. The organic solvent containing the ECL moiety penetrates the pores of the carrier and, upon evaporation of the organic solvent, the ECL moiety becomes trapped or encased in the interior of the carrier. When the bead is solvated in an aqueous solvent, most or all of the ECL moiety remains encased within the carrier. In certain embodiments, the carrier is a polystyrene bead. In some embodiments, the ECL moiety can be incorporated into a gel by forming the gel in a solution comprising the ECL moiety. In some embodiments, the ECL moiety can be incorporated into a micelle by forming the micelle in a solution comprising the ECL moiety. In some embodiments, the ECL moiety can be incorporated into a liposome by forming the liposome in a solution comprising the ECL moiety.

In some embodiments, the ECL moiety can be trapped inside a carrier without substantial loss into the surrounding media. Loss of ECL moiety to the surrounding liquid phase may be unwanted during preparation and use. The carrier's ability to trap the ECL moiety can be fundamentally described by an important physical constant termed a partition coefficient. The partition coefficient is K=C carrier/C liquid, where C carrier is the concentration of the moiety imbibed with the carrier and C liquid is the concentration of moiety not imbibed.

With a system of two phases (carrier and liquid), a moiety with a partition coefficient greater then one shows a preference to the carrier phase. High values of partition coefficient indicate a strong preference for the carrier phase. Conversely, a moiety with a partition coefficient less then one would prefer the liquid phase. A low partition coefficient system which initially had high levels of ECL moieties within the carrier would lose moieties to the surrounding liquid phase.

In some embodiments, the partition coefficient between the carrier and an aqueous solvent is greater than about 2. In some embodiments, the partition coefficient between the carrier and an aqueous solvent is greater than about 10. In some embodiments, the partition coefficient between the carrier and an aqueous solvent is greater than about 100. There are several chemical and physical designs to achieve a high partition coefficient. (1) The moiety can be held to the carrier by coulombic attraction. In such case, the ECL moiety can have a net positive charge and the carrier has a net negative charge. (2) In some embodiments, the solubility of the ECL moiety can be much greater in the carrier phase. For example, the ECL moiety is not soluble in water and is soluble in a lypophilic polystyrene carrier. (3) In some embodiments, the ECL moiety can be trapped within the carrier because the microscopic porosity of the carrier is smaller then the moiety diameter. (4) In some embodiments, the moiety can be bounded to the carrier though covalent bonds.

F. Methods of Detecting an Analyte of Interest

The application provides various methods of detecting an analyte of interest contained within a sample. In some embodiments, the analyte of interest can be linked to a carrier, e.g., a first carrier. The analyte of interest can be present on the surface of the carrier thus facilitating its access to a specific binding partner. In some embodiments, the analyte of interest can not be linked to any carrier. In some embodiments, the analyte of interest can be present in solution.

The methods described herein provide for at least one specific binding partner capable of binding specifically to the analyte of interest. In some embodiments, the at least one specific binding partner can be linked to a carrier. In this embodiment the sample can be linked to a second carrier.

In some embodiments, at least one specific binding partner can be a binding protein capable of specifically binding to the molecule of interest. The binding partner can be linked to a carrier. In this embodiment the sample can be linked to a second carrier.

In some embodiments, at least one specific binding partner can be an oligonucleotide or a nucleic acid capable of specifically binding to the analyte of interest. The binding partner can be linked to a carrier. In this embodiment the sample can be linked to a second carrier.

In some embodiments, the application provides for two specific binding partners, i.e., a first and a second specific binding partner, both of which specifically bind to the analyte of interest. The two specific binding partners can both be linked to a carrier. Thus, in certain embodiments, a first specific binding partner can be linked to a first carrier and a second specific binding partner can be linked to a second carrier. In this embodiment, the sample can not be linked to any carrier. It is also contemplated that the same specific binding partner can be linked to both the first and second carrier. In some embodiments, a polyclonal antibody which specifically binds the analyte of interest could be linked to both the first and second carrier. In some embodiments, the analyte of interest could contain multiple copies of an epitope recognized by a monoclonal antibody or, where the analyte is a nucleic acid, it could contain multiple repeats of a sequence recognized by a probe linked to both the first and second carrier. In certain embodiments, at least one of the specific binding partners can be an antibody. It is also contemplated that both specific binding partners can be antibodies. The application also encompasses embodiments in which one specific binding partner can be an antibody and a second specific binding partner can be a specific binding protein.

In some embodiments, at least one specific binding partner can be an oligonucleotide that hybridizes with the molecule of interest in the sample. As with antibodies, it is contemplated that both specific binding partners can be oligonucleotides or other nucleic acids that hybridize with the molecule of interest in the sample.

ECL moieties can be detected by methods well known in the art including, for example, emission and absorption spectroscopy, e.g., ultraviolet absorption, infrared absorption, and fluorescence emissions; atomic absorption, electrochemical, e.g. anodic stripping voltametry; neutron activation and chemical methods. In certain embodiments photoluminescence, chemiluminescence and electrochemiluminescence methods are used. In some embodiments, the presence of the chemical moiety can be determined by inducing the ECL moiety to emit electromagnetic radiation and detecting the emitted radiation. In some embodiments, the ECL moiety can be induced to emit electromagnetic radiation by exposing the reagent mixture to electromagnetic, chemical or electrochemical energy. In some embodiments, the ECL moiety can be induced to emit electromagnetic radiation by exposing the reagent mixture to chemical or electrochemical energy. In certain embodiments, a co-reactant is added to aid in detecting the ECL moiety, e.g., TPrA.

$Ru(bpy)_3^{2+}$ can be determined at very low concentrations using luminescence techniques. Using the oxidative reduction method, it is possible to detect $Ru(bpy)_3^{2+}$ at concentrations of $5 \times 10^{-8}$ M. Sodium oxalate (1 mM) in phosphate buffer pH 5.0, can be used with a potential pulsed at 0 to +1.4 volts versus a saturated calomel reference electrode for 5 to 10 second intervals. Using 18 mM $Na_2S_2O_8$ and 0.1 M tetra-n-butyl ammonium tetrafluoroborate in $CH_3CN:H_2O$ (1:1 v/v), $Ru(bpy)_3^{2+}$ concentrations as low as $10^{-13}$ M can be detected (see, e.g., U.S. Pat. Nos. 6,140,138; 5,731,089; 5,714,089).

The present application also provides methods for employing ECL moieties in assays for detecting an analyte of interest comprising: (a) forming a complex having the formula:

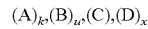

wherein, in certain embodiments, A is an ECL moiety which can be induced to repeatedly emit electromagnetic radiation by direct exposure to an electrochemical energy source; B is a first carrier (linked to a specific binding partner of the analyte of interest) which is associated with A; C is a sample which may contain the analyte of interest, B being linked to the analyte of interest via the binding partner of the analyte of interest; and D is a second carrier which can be directly linked to the analyte of interest or linked to the analyte of interest via a second specific binding partner of the analyte of interest; k, u, and x are each an integer equal to or greater than 1; (b) separating the complex formed in (a) from other components of the composition; (c) inducing the ECL moiety to repeatedly emit electromagnetic radiation by directly exposing the moiety to electrochemical energy; and (d) detecting the emitted electromagnetic radiation and thereby determining the presence of the analyte of interest.

In certain embodiments, the present method can be a competitive binding assay, e.g., a competitive inhibition assay (see, e.g. Janeway et al Immunobiology, Garland Publishing, New York 2001). In some embodiments of this assay, a known quantity of the analyte of interest or an analog of the analyte of interest can be linked (the term "linked" comprises both covalent and noncovalent linkages) to a carrier that does not comprise an ECL moiety, for example, a magnetic bead. A binding partner for the analyte of interest can be linked to a second carrier, for example, a polystyrene bead, which does comprise an ECL moiety. In the absence of added analyte of interest, a complex will form between the analyte of interest linked to the first carrier and the binding partner for the analyte of interest linked to the second carrier, effectively linking the first carrier to the second carrier. The amount of ECL moiety associated with this complex can be measured by techniques known in the art. The presence of the analyte of interest in a sample can then be detected by its ability to decrease the amount of complex formed by competition with the carrier-linked molecule of interest for binding to the second-carrier-linked binding partner. In certain embodiments, the amount of the analyte of interest in a sample can be quantified by comparison with standard curves using samples comprising known amounts of the molecule of interest.

In some embodiments, the application provides a sandwich-type binding assay for detecting an analyte of interest. In some embodiments of this assay, a first binding partner of the analyte of interest can be linked to a first carrier, for example a magnetic bead. A second binding partner of the analyte of interest can be linked to a second carrier, for example a polystyrene bead, which can comprise an ECL moiety. In the presence of a sample containing the analyte of interest, complexes comprising both the first carrier and the second carrier can form. The amount of ECL moiety associated with this complex, which is proportional to the amount of the biological material of interest in the sample, can be measured by techniques known in the art. In certain embodiments, the amount of the analyte of interest in a sample can be quantified by comparison with standard curves using samples comprising known amounts of the molecule of interest.

In some embodiments, the application provides a direct binding method for detecting an analyte of interest in a sample. In some embodiments of this method, molecules in the sample can be linked to a first carrier, for example, a magnetic bead. A binding partner of the analyte of interest can be linked to a second carrier, for example a polystyrene bead, which can comprise an ECL moiety. If a sample contains the analyte of interest, complexes comprising both the first carrier and the second carrier can form. The amount of ECL moiety associated with this complex, which is proportional to the amount of the biological material of interest in the sample, can be measured by techniques known in the art. In certain embodiments, the amount of the analyte of interest in a sample can be quantified by comparison with standard curves using samples comprising known amounts of the molecule of interest.

Many variations on these types of binding assays are known to those skilled in the art and are compatible with the present methods.

There are many methods for quantifying the amount of ECL moiety present. The rate of energy input into the system can provide a measure of the ECL moiety. Suitable measurements include, for example, measurements of electric current when the ECL moiety is excited electrochemically, the rate of reductant or oxidant utilization when the ECL moiety is excited chemically, or measurements of the absorption of electromagnetic energy in photoluminescent techniques. The ECL moiety can also be detected by measuring the emitted electromagnetic radiation. All of these measurements can be made either as continuous, rate-based measurements, or as cumulative methods which accumulate the signal over a long period of time. Rate-based measurements can be made using photomultiplier tubes, photodiodes, or phototransistors that produce electric currents proportional in magnitude to the incident light intensity. Cumulative methods can involve the integration of rate-based data or the use of photographic film to directly provide cumulative data.

The application also provides for the isolation of a complex comprising the analyte of interest, at least one carrier, and an ECL moiety. In some embodiments, a magnetic field can be used to separate the complex, e.g., when the at least one carrier is a magnetic bead. In some embodiments, separation of the complex can be achieved by precipitation, e.g., by the force of gravity when the mass of the complex is greater than the mass of the individual components. In some embodiments, a filter can be used to separate the complex from other components of the composition. The filter can, for example, have a pore size small enough to retain the complex, but large enough to permit uncomplexed material to pass through. In some embodiments, a size exclusion column can be used to separate the complex. Other properties that distinguish the complex from other components of the composition can also be used, for example, hydrophobicity or affinity for other binding partners.

G. Diseases and Conditions

In certain embodiments, the analyte of interest can be a marker associated with a disease or condition. The application thus provides a method of detecting a marker associated with a disease or condition and thereby diagnosing a subject having a disease or condition. In some embodiments, the application provides a method to monitor the progression of a disease or condition by monitoring the presence or quantity of a marker associated with a disease or condition. In some embodiments, the application provides a method for monitoring the effectiveness of therapy used to treat a disease or condition by monitoring the presence or quantity of a marker associated with a disease or condition.

The disease or condition can include an infectious disease caused by an infectious agent, e.g., bacteria, fungi, parasites, viruses, or prions. Examples of bacterial pathogens include *B. anthracis, E. coli, S. pneumoniae, S. pyogenes, S. bovis, S. agalactiae, S. aureus, S. epidermidis N. meningitidis, M. tuberculosis*. Examples of viral infections include smallpox, severe acute respiratory syndrome (SARS), human immunodeficiency virus (HIV), Epstein-Barr virus(EBV), hepatitis B, hepatitis C, rhinovirus, influenza, respiratory syncytia virus(RSV), measles, polio, herpes simplex virus-1 (HSV-1) and herpes simplex virus-2 (HSV-2). Examples of parasites include *Plasmodium falciparum, P. vivax, P. malaria, Toxoplasma gondii. Trypanosoma cruzi*, and *Giardia lamblia*.

The disease can be cancer or an auto-immune disease. Markers associated with various cancers which can be analytes of interest, include mutant cyclin-dependent kinase 4 of melanoma; p17 protein of melanoma; gp 100 of melanoma; melanoma associated antigen-1 (MART-1) (Melan-A) of melanoma (PCT publication WO94/21126); p15 protein of melanoma; tyrosinase of melanoma (PCT publication WO94/14459); melanoma associated antigen (MAGE) 1, 2 and 3 of melanoma, thyroid medullary, small cell lung cancer, colon and/or bronchial squamous cell cancer (PCT/US92/04354); melanoma associated antigen-Xp (MAGE-Xp) (U.S. Pat. No. 5,587,289); B melanoma antigen (BAGE) of bladder, melanoma, breast, and squamous-cell carcinoma (U.S. Pat. No. 5,571,711 and PCT publication WO95/00159); G antigen (GAGE) (U.S. Pat. No. 5,610,013 and PCT publication WO95/03422); renal tumor antigen (RAGE) family (U.S. Pat. No. 5,939,526); preferentially expressed antigen in melanoma (PRAME) (formerly DAGE; PCT publication WO96/10577); melanoma ubiquitous mutated protein (MUM-1/LB-33B) (U.S. Pat. No. 5,589,334); neuroblastoma amplified protein (NAG) (U.S. Pat. No. 5,821,122); FB5 (endosialin) (U.S. Pat. No. 6,217,868); PSMA (prostate-specific membrane antigen) (U.S. Pat. No. 5,935,818); gp75 of melanoma; oncofetal antigen of melanoma; carbohydrate/lipids such as mucin of breast, pancreas, and ovarian cancer; GM2 and GD2 gangliosides of melanoma; oncogenes such as mutant p53 of carcinoma; mutant ras of colon cancer; erythroblastic leukemia viral oncogene homolog 2 (HER2/neu) proto-oncogene of breast carcinoma; and viral products such as human papillomavirus proteins of squamous cell cancers of cervix and esophagus. Markers associated with autoimmune diseases include antibodies that specifically bind chromatin associated with systemic lupus erythematosus, the presence of human leukocyte antigen (HLA) allele DR2 (associated with multiple sclerosis), DR3 (associated with Graves disease) or DR4 associated with rheumatoid arthritis (Janeway et al. Immunobiology, Garland Publishing, New York 2001).

H. Kits

In certain embodiments, the application provides a kit for detecting an analyte of interest in a sample. The kit can comprise a first carrier comprising at least one ECL moiety, a second carrier, at least one specific binding partner of the analyte of interest linked to at least one of the first and second carriers, at least one container, and, optionally, instructions. In certain embodiments the kit can comprise 2 or more ECL moieties.

EXAMPLES

Chemicals and Materials: Tris(2,2'-bipyridyl)ruthenium (II) dichloride hexahydrate ($Ru(bpy)_3Cl_2 \cdot 6-H_2O$), trifluoroacetic acid (TFAA,99%), silver tetrafluoroborate ($AgBF_4$, 98%), and tri-n-propylamine (TPrA, 99+%) obtained from Aldrich (Milwaukee, Wis.); lithium tetrakis(pentafluorophenyl)borate ($Li[(B(C_6F_5)_4)] \cdot nEt_2O$, n=2-3) obtained from Boulder Scientific Co. (Mead, Colo.); tetrabutylammonium tetrafluoroborate (($TBA)BF_4$, electrochemical grade) obtained from Fluka (Milwaukee, Wis.); tris(hydroxymethyl)aminomethane (Tris, ultrapure) from Life Technologies (Rockville, Md.); 1-ethyl-3-(3-dimethylaminopropyl) carbodiimide hydrochloride (EDAC, SigmaUltra), N-hydroxysuccinimide (NHS), fluorescein biotin (90%), 1-methylimidazole, and DNA hybridization buffer (PerfectHyb™ plus) obtained from Sigma (St. Louis, Mo.); sodium hydroxide (GR), hydrochloric acid (GR), sodium chloride (GR), ethyl ether (anhydrous), acetonitrile (HPLC), tetrahydrofuran (THF, GR), and ethylenedinitrilotetraacetic acid (EDTA) obtained from EM (Gibbstown, N.J.); avidin (NeutrAvidin), D-biotin (ImmunoPure®) and biotin-PEO-LC-amine obtained from Pierce (Rockford, Ill.); and methanol (spectroanalyzed grade) obtained from Fisher (Fairlawn, N.J.) were used without further purification unless otherwise stated. Carboxylate polystyrene microspheres/beads (PSB, 10 µm in diameter, 2.6% (w/w) aqueous suspension with $6.5 \times 10^4$ beads/µL) and streptavidin coated superparamagnetic polystyrene beads (referred to as magnetic beads or MB, (a) 1.0 µm in diameter, 10 mg/mL aqueous suspension with about $9.5 \times 10^6$ beads/µL; (b) 2.8 µm in diameter, 10 mg/mL aqueous suspension with about $6.5 \times 10^5$ beads/µL) were purchased from PolySciences Inc. (Warington, Pa.) and Dynal Biotech Inc. (Lake Success, N.Y.), respectively. Synthetic 23-mer single-stranded DNA (ssDNA) oligonucleotides derived from the *Bacillus anthacis* (Ba813) were obtained from Qiagen Operon (Alameda, Calif.) and had the following sequences: (a) probe, 5'-[biotin-TEG]-AACGA TAGCT CCTAC ATTTG GAG-3' (p-ss-DNA, M.W.=7617 g/mol; SEQ ID NO: 1); (b) target or complementary, 5'-[biotin-TEG]-CTCCA MTGT AGGAG CTATC GTT-3' (t-ssDNA, M.W.=7608 g/mol; SEQ ID NO: 2); (c) non-complementary, 5'-[biotin-TEG]-TTAAC ACCTT AGCGA CGGCT AGT-3' (nc-ssDNA, MW=7593 g/mol; SEQ ID NO: 3); and (d) 2-base pairs mismatched oligomer sequence, 5'-[biotin-TEG]-CTCCA MCGT AGGAG TTATC GTT-3' (2-bp-m-ssDNA; SEQ ID NO: 4), in which biotin-TEG contained a 16-atom mixed polarity spacer based on a triethylene glycol and used to reduce the steric hindrance between the biotinylated DNA and surface confined avidin/streptavidin interactions. Unless otherwise stated, all solutions were freshly prepared with 18 M.OMEGA.-cm deionized Milli-Q water (Millipore Corp., Bedford, Mass.)

ECL and Electrochemical Measurements. A three-electrode cell system was used, with a 2.2 mm diameter Pt disk, 2.0 mm diameter Au or 3.0 mm diameter glassy carbon (GC) disk as the working electrode, a Pt wire as the counter electrode and a Ag/Ag+ (10 mM $AgBF_4$ and 50 mM $TBABF_4$ in MeCN) as the reference electrode. All electrodes were carefully cleaned before each experiment. The cleaning steps included: immersing the working electrodes into a chomic acid solution, polishing with a 0.05 µm alumina slurry (Buehler Ltd., Lake Bluff, Ill.), washing with copious amounts of water, rinsing with MeCN, and replacing the porous Vycor tip and the glass tube for the reference electrode. A 5 mL disposable glass vial served as the electrochemical cell. To exclude the possibility of the ECL signal being generated from a $Ru(bpy)_3^{2+}$ contaminated system, virgin glassware and electrodes were used whenever necessary. The ECL intensities, along with the cyclic voltammograms (CV), were measured simultaneously with a home-built potentiostat combined with a photomultiplier tube (PMT, Hamamatsu R4220p, Japan) installed under the electrochemical cell. A voltage of −750 V was supplied to the PMT with a high-voltage power supply (Bertan High Voltage Corp., Series 225, Hicksville, N.Y.).

All measurements were conducted at a temperature of 20±2° C., unless otherwise stated.

Example 1

Synthesis of Ru(bpy)$_3^{2+}$ Containing ECL Labels

Tris(2,2'-bipyridyl) ruthenium(II) tetrakis(pentafluorophenyl)borate (Ru(bpy)$_3$[B(C$_6$F$_5$)$_4$]$_2$) was used as the ECL label in the present study, because, as shown in the next sections, this complex can be effectively loaded into polystyrene beads using a suitable organic solution and maintained entrapped within the beads during a series of modification of the beads in aqueous solutions. In other words, Ru(bpy)$_3$[B(C$_6$F$_5$)$_4$]$_2$ is sufficiently soluble in organic solvents but completely insoluble in aqueous solutions. Another reason to choose Ru(bpy)$_3$[B(C$_6$F$_5$)$_4$]$_2$ as the ECL label was the fact that the Ru(bpy)$_3^{2+}$ moiety of the complex has a very high ECL efficiency. Ru(bpy)$_3$[B(C$_6$F$_5$)$_4$]$_2$ was prepared by a metathesis reaction between Ru(bpy)$_3$Cl$_2$ and Li[B(C$_6$F$_5$)$_4$]-nEt$_2$O (n=2-3) in water. The precipitate was washed with water, recrystallized from an acetonitrile/water solution, and dried under vacuum.

Example 2

Figure 4:
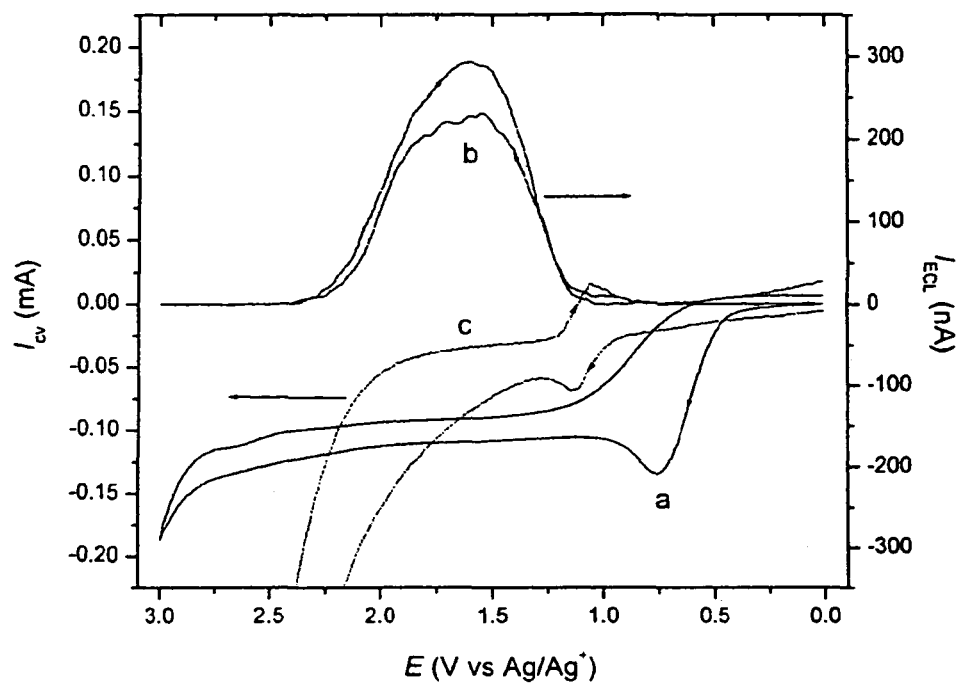
FIG. 4 shows (a) cyclic voltammetric (CV) and (b) ECL responses obtained from 0.10 μM $Ru(bpy)_3[B(C_6F_5)_4]_2$ in acetonitrile (MeCN) containing 0.10 M $(TBA)BF_4$ electrolyte-0.10 M tripropylamine (TPrA) coreactant at a 2.2 mm diameter Pt electrode with a scan rate of 50 mV/s. For comparison, CV of 1.0 mM $Ru(bpy)_3[B(C_6F_5)_4]_2$ in MeCN containing 0.10 M (TBA) $BF_4$ in the absence of TPrA is presented in (c). The experimental conditions in (c) were as in (a) and (b), but the CV current was multiplied by 10.

Electrochemical and ECL Behavior of Ru(bpy)$_3^{2+}$ in MeCN Using TPrA as a Coreactant The cyclic voltammetric and ECL responses of 0.10 μM Ru(bpy)$_3$[B(C$_6$F$_5$)$_4$]$_2$ in MeCN containing 0.10 M (TBA)BF$_4$ electrolyte-0.10 M TPrA coreactant at a Pt electrode at a scan rate of 50 mWs are shown in FIG. 4. TPrA starts to oxidize at potentials around 0.5 V vs Ag/Ag$^+$, and shows a maximum oxidation peak at about 0.75 V vs Ag/Ag$^+$ (FIG. 4a). When the electrode is scanned to a potential more positive than 1.1 V vs Ag/Ag$^+$ where the Ru(bpy)$_3^{2+}$ is oxidized to Ru(bpy)$^{3+}$ Ru(bpy)$^{3+}$ (FIG. 4c), the ECL is produced (FIG. 4b). The ECL intensity continuously increases with increasing potential, finally forming a broad peak with a half-wave width of about 700 mV and a peak potential at about 1.6 V vs Ag/Ag$^+$. On the reverse scan, a larger ECL intensity and similar peak position is observed. Note that the oxidation potential of Ru(bpy)$_3^{2+}$ can slightly shift positive in the presence of TPrA, since the ECL peak potentials are more positive in comparison with the oxidation potential of Ru(bpy)$_3^{2+}$ in the absence of TPrA (FIGS. 4b and c). As expected, a change in the counter ions of Ru(bpy)$_3^{2+}$ complexes, e.g., from B(C$_6$F$_5$)$_4^-$ to ClO$_4^-$, did not change the ECL behavior. In contrast to the case in aqueous solution, where a pre-wave ECL appeared in the potential region of TPrA oxidation due to the formation of excited state Ru(bpy)$_3^{2+*}$ on reaction of TPrA$^{*+}$ with Ru(bpy)$_3^+$ (formed by reaction of Ru(bpy)$_3^{2+}$ with TPrA*) when a μM level of Ru(bpy)$_3^{2+}$ was used, (Miao, Choi and Bard, 2002, J. Am. Chem. Soc. 124:14478) no noticeable corresponding ECL signal was found in MeCN. This suggests that under the present experimental conditions, either the life time of TPrA$^{*+}$ in MeCN is shorter than in neutral aqueous solutions, or TPrA$^{*+}$ is not energetically powerful enough to oxidize Ru(bpy)$_3^+$ to Ru(bpy)$_3^{2+*}$. Apart from this, we conclude that the ECL mechanism developed in aqueous solutions using TPrA as a coreactant is operative in MeCN.

Figure 5A:
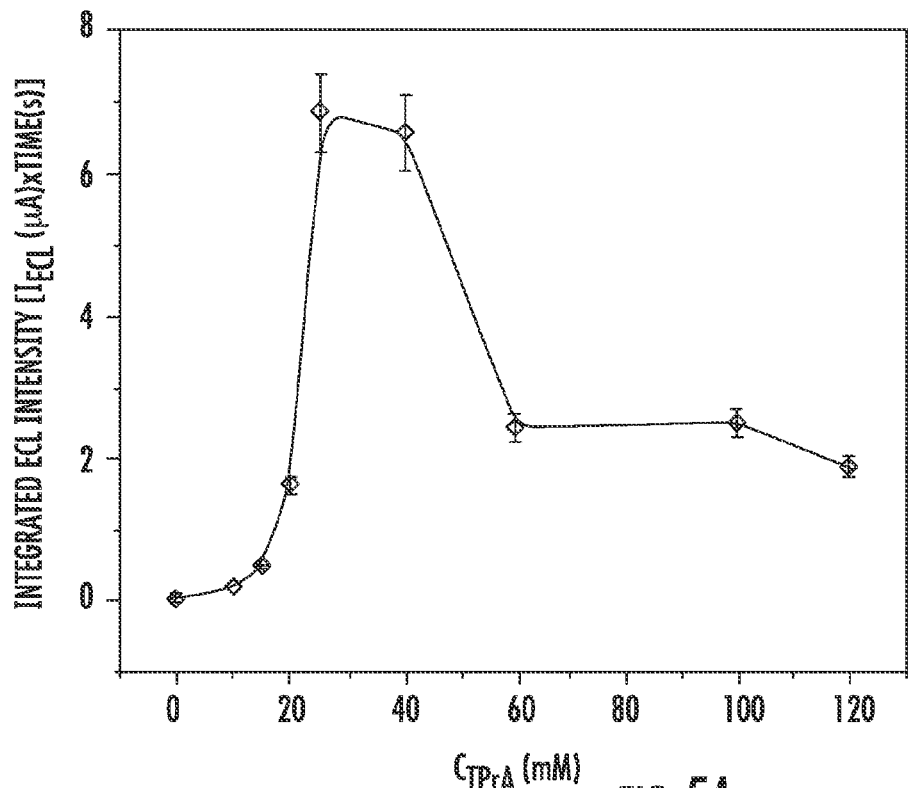
FIG. 5A-B shows FIG. 5A TPrA and FIG. 5B TPrA-trifluoroacetic acid (TFAA) concentration effect on ECL intensity. All samples contained 0.10 μM $Ru(bpy)_3[B(C_6F_5)_4]_2$ and 0.10 M $(TBA)BF_4$ in MeCN. The working electrode was a Pt electrode having a 2.2 mm diameter. The scan rate was 50 mV/s.
Figure 5B:
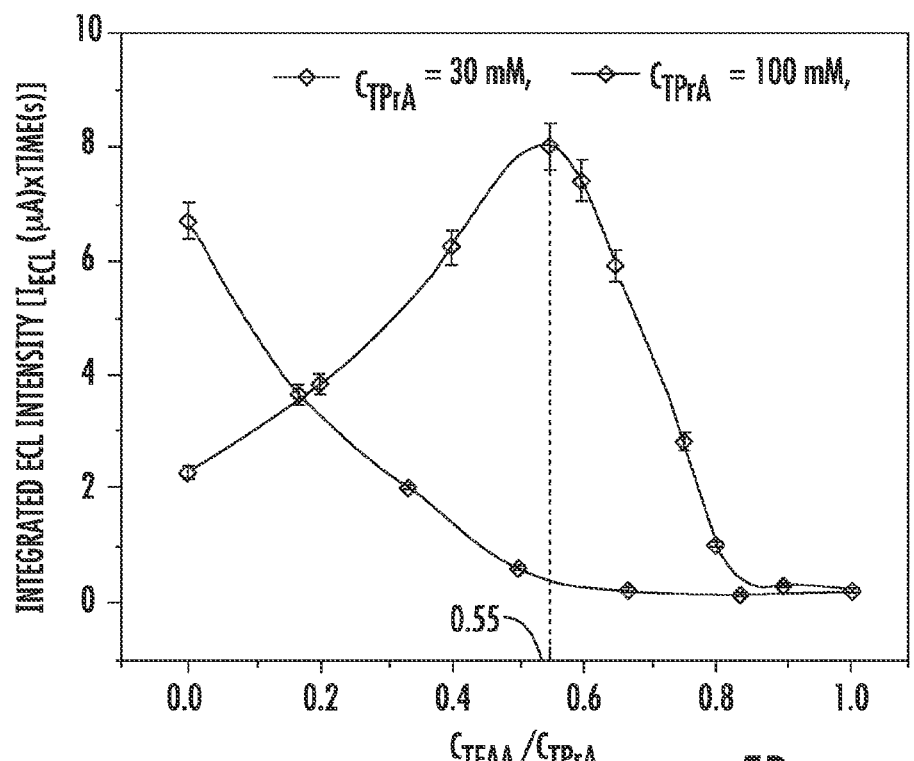

The ECL intensity as a function of TPrA concentration is shown in FIG. 5A, where the highest ECL intensity region corresponds to a TPrA concentration of 30 mM. As would be expected, on the basis of the ECL-pH dependence study in aqueous solution, (Leland et al. 1990, J. Electrochem. Soc. 137:3127) by adding trifluoroacetic acid (TFAA) into a Ru(bpy)$_3^{2+}$/TPrA/MeCN solution, hence changing the acidity of the solution, the ECL intensity is changed (FIG. 5B). A combination of 100 mM TPrA with 55 mM TFAA gave the largest ECL response.

The ECL intensity and stability were also affected by the electrode material used. Pt and Au electrodes showed similar responses; the ECL was stable over several potential cycles, with a slightly smaller photocurrent density found at a Pt compared to an Au electrode. At a GC electrode, however, only the forward scan of the first potential cycle produced light. After polishing of the GC electrode, the light arose again, suggesting the electrode surface had been blocked by a film of some kind. The relative ECL intensity, obtained from a MeCN solution containing 0.10 μM Ru(bpy)$_3$[B(C$_6$F$_5$)$_4$]$_2$-0.10 M TPrA-0.055 M TFM-0.10 M (TBA)BF$_4$ during the first potential cycle between 0 and 3.0 V vs Ag/Ag+ at a scan rate of 50 mV/s, at Au, Pt and GC electrode had a ratio of 100:93:61.

Figure 6:
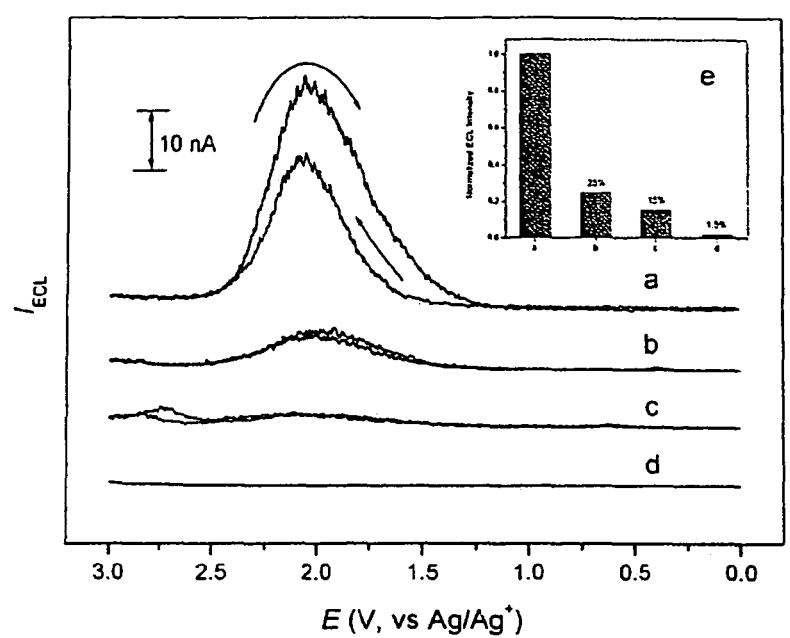
FIG. 6 shows the elimination of ECL background for the TPrA-MeCN system. In (a) 0.10 M TPrA and 0.10 M (TBA)$BF_4$-MeCN was used. In (b), the same conditions as in (a) were used with the addition of 0.055 M TFM. In (c) the same conditions as in (b) were used with the addition of 1.0% (v/v) $H_2O$. In (d) 0.10 M (TBA) $BF_4$-MeCN was used.

Interestingly, even in the absence of Ru(bpy)$_3^{2+}$, a TPrA in acetonitrile solution with 0.10 M (TBA)BF$_4$ can also produce an ECL signal (FIG. 6a). Purification of the TPrA and MeCN by distillation, changing the electrolyte from (TBA)BF$_4$ to (TBA)ClO$_4$ or using a newly opened electrochemical grade electrolyte, using virgin glassware and electrodes, and covering the Pt counter electrode with a glass tube coated with or without a layer of black plastic, did not change the result. The ECL had a peak potential value of 2.1 V vs Ag/Ag$^+$, which is a 500 mV shift compared to that obtained in the presence of 0.10 μM Ru(bpy)$_3^{2+}$ (FIG. 4b). As shown previously in FIG. 5A, in the absence of TPrA, a Ru(bpy)$_3^{2+}$ in MeCN solution with 0.10 M (TBA)BF$_4$ did not give an observable ECL response on the same intensity scale with a scan only to positive potentials. Thus, the ECL signals shown in FIG. 6a must originate from TPrA, and are probably due to the charge-transfer reaction inverse photoemission (CTRIP) associated with TPrA* free radicals (Murakoshi et al. 1992, J. Phys. Chem. 96:4593; Uosaki et al. 1991, J. Phys. Chem. 95:779; Uosaki et al. 1990, Chem. Lett. 7; 1159; McIntyre et al. 1987, J. Electroanal. Chem. Interfac. Electrochem. 228:293; McIntyre et al. 1986, Phys Rev Lett. 56:651; McIntyre et al. 1985, J. Electroanal. Chem. Interfac. Electrochem 196:199; Murakoshi et al. 1993, Conden Mar Mater. Phys. 47:2278; Ouyang and Bard 1988, J. Phys. Chem. 92:5201; Ouyang and Bard 1987, J. Phys. Chem. 91:4058). The integrated ECL intensity obtained from FIG. 6a, which is about 12% of that obtained from FIG. 4b, is significant, since in the absence of TPrA, the residual photocurrent measured from a 0.10 M (TBA)BF$_4$/MeCN solution is significantly less (FIG. 6d). The background TPrA-related ECL signals was suppressed dramatically by adding TFAA to the solution (FIG. 6b), and a further elimination of the "unwanted" signals was achieved by a addition of 1% (v/v) H$_2$O into the 0.10 M TPrA-0.055 M TFM-0.10 M (TBA)BF$_4$ MeCN solution (FIG. 6c). FIG. 6 displays the relative ECL intensities obtained from FIGS. 6a to 6d (see 6e).

Example 3

Loading ECL Labels into Polystyrene Beads

Carboxylate polystyrene beads having a 10 μm diameter were separated from an appropriate volume (0.10-1.0 mL) of 2.6% (w/w) polystyrene beads suspension with an Eppendorf 5415D centrifuge (Brinkmann Instruments, Inc. Westbury, N.Y.) at 10 k rpm for 5 minutes, and then washed once with 1 mL of water.

Figure 2A:
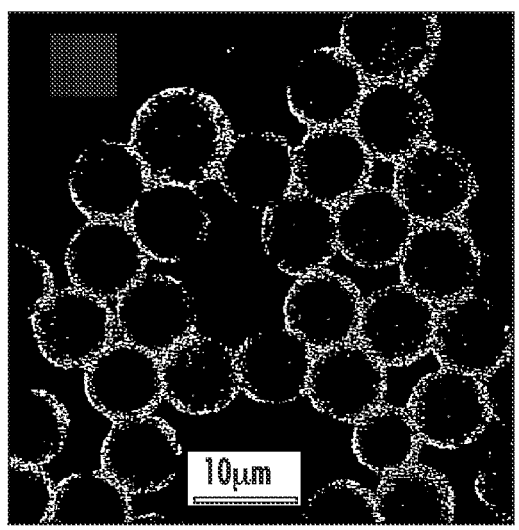
FIG. 2A-B shows fluorescent images of carboxylate polystyrene beads having a 10 μm diameter.

The beads were dried under vacuum at 60° C. for 1 hour, followed by adding 1.5 mL of the ECL label Ru(bpy)$_3$[B(C$_6$F$_5$)$_4$]$_2$-saturated (0.7 mM) 5% THF-95% MeOH (v/v) solution into a 2 mL microcentrifuge tube containing the PSB. The mixture was rotated with a Dynal™ sample mixer (Dynal Biotech Inc.) at 20 rpm for 2 hours, followed by centrifugation and washing with 50% MeOH-50% H$_2$O (v/v) twice. The resulting ECL label-containing yellowish polystyrene beads, designated as Ru(II)<PSB, were further dried under vacuum at 60° C. for 1 hour. During the course of the above treatments, the polystyrene beads were first swelled in the ECL label containing 5% THF-95% MeOH organic solution, allowing the water-insoluble ECL labels to diffuse into the polymer matrix, where they were entrapped when the organic solvents were removed from the beads by vacuum evaporation. The effective loading of the ECL labels into the polystyrene beads can be visually verified via the fluorescent image (FIG. 2A) taken with a Nikon Eclipse TE 300 inverted microscope (Nikon Instruments Inc., Melville, N.Y.) coupled with a Magnafire-Model S99806 Olympus America CCD camera (Olympus America, Melville, N.Y.). A typical loading capacity of $7.5 \times 10^9$ Ru(bpy)$_3$[B(C$_6$F$_5$)$_4$]$_2$ molecules per bead was estimated on the basis of the ECL data obtained from Ru(II)<PSB dissolved in MeCN and a standard Ru(bpy)$_3$[B(C$_6$F$_5$)$_4$]$_2$ solution using TPrA as a coreactant.

Example 4

Immobilizing Avidin on the Surface of Ru(II)<PSB

Figure 2B:
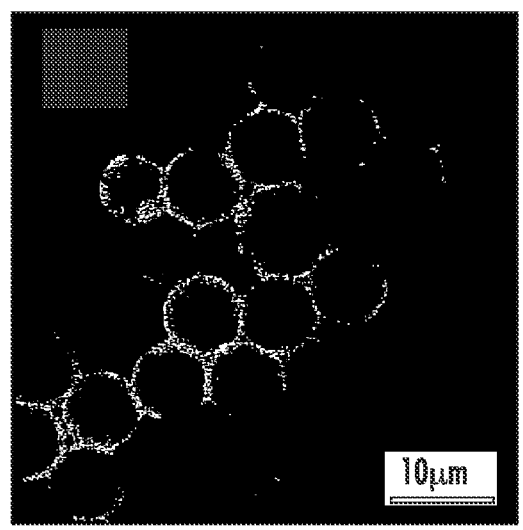
Figure 10A:
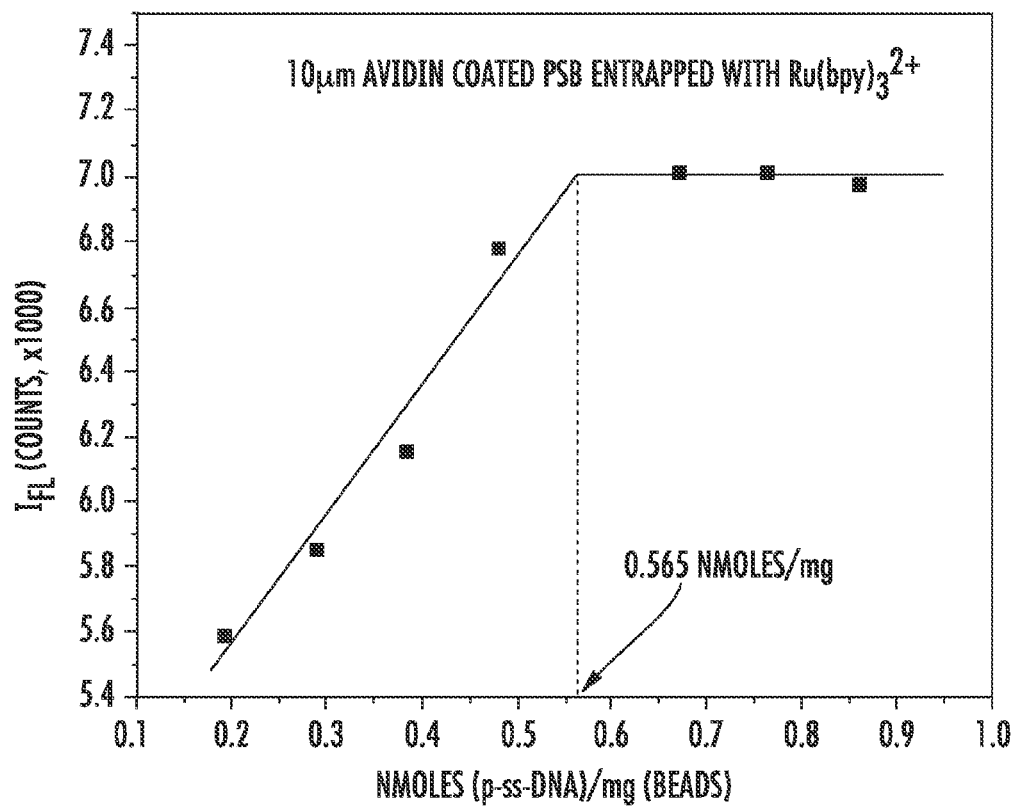
FIG. 10A-C shows the binding capacities of FIG. 10A 10 μm diameter streptavidin coated polystyrene beads entrapped with $Ru(bpy)_3^{2+}$, FIG. 10B 1.0 μm diameter streptavidin coated magnetic beads, and FIG. 10C 2.8 μm diameter streptavidin-coated magnetic beads for a biotinylated 23-mer-ss DNA (p-ssDNA) obtained from fluorescein biotin titration experiments.
Figure 10B:
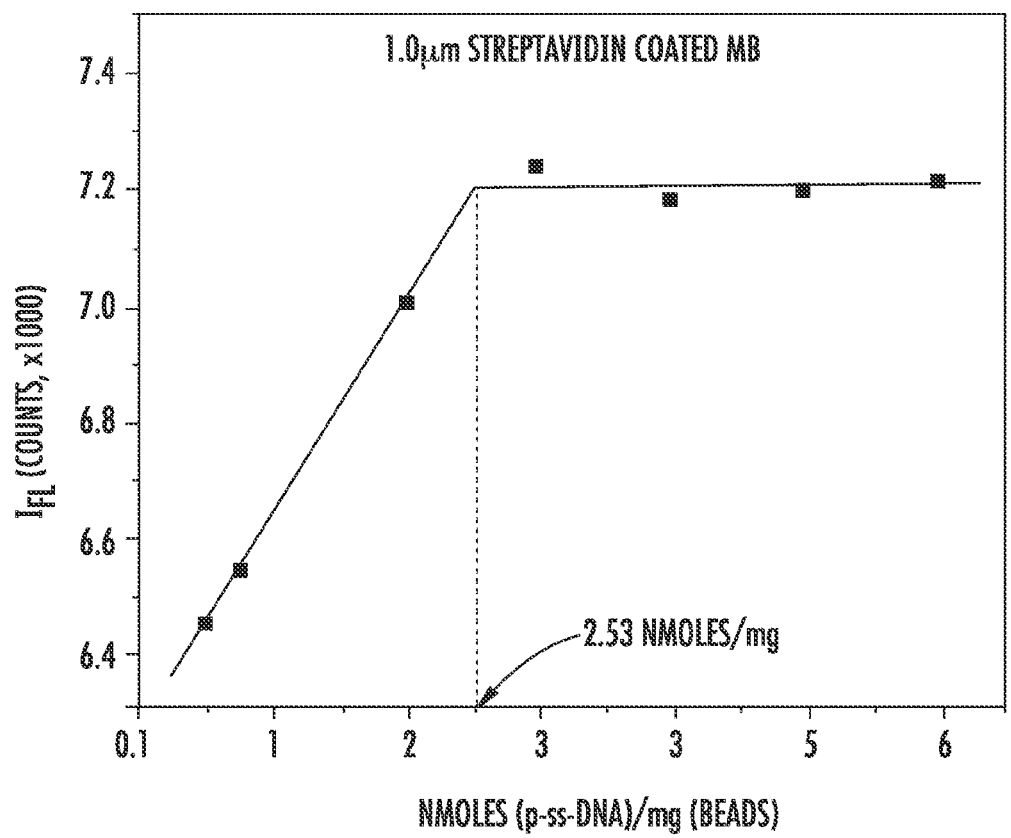
Figure 10C:
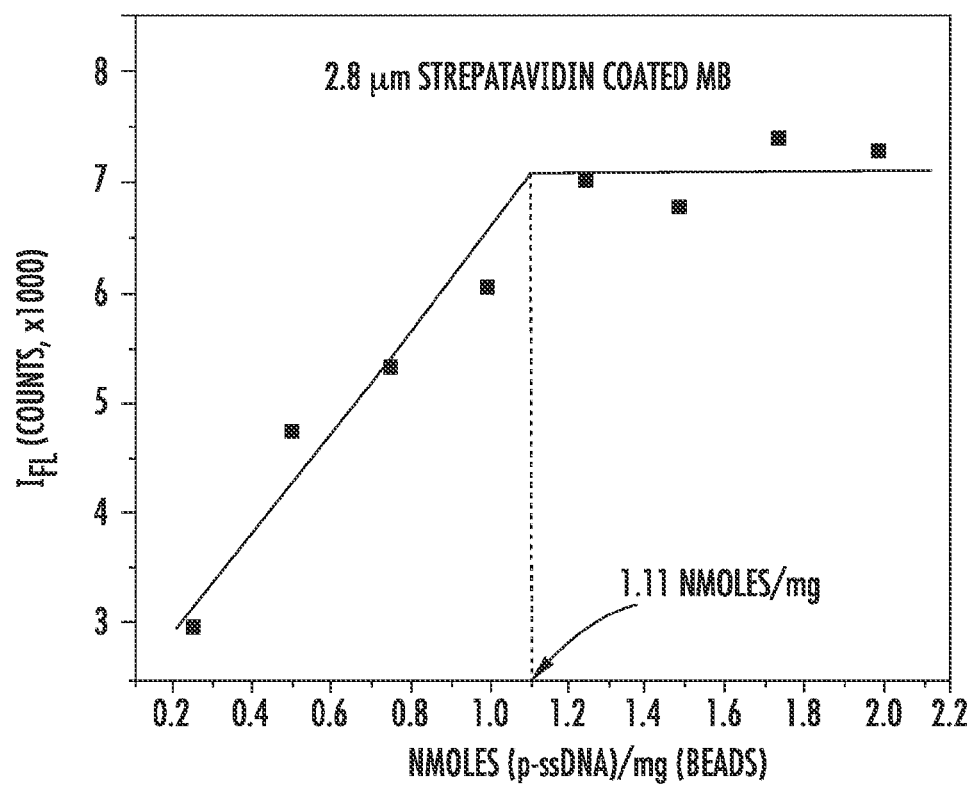

A layer of avidin was covalently attached to the surface of Ru(II)<PSB via the formation of Ru(II)<PSB—CO—NH-avidin, by immersing the beads into 1.5 mL of freshly prepared 25 µM avidin in 0.10 M 1-methylimidazole buffer (pH 7) containing 0.10 M EDAC and 0.10 M NHS, and rotating the mixture at about 40 rpm for 1 h. The newly formed avidin coated Ru(II)<PSB, designated as Ru(II)<PSB/Avidin, were centrifuged from the reaction solution at 5-10 k rpm for 5 min, and washed with 1 mL of "1× B&W buffer" (1× buffer & wash solution, 5 mM Tris-HCl (pH 7.5)+0.5 mM EDTA+1.0 M NaCl) three times. The final Ru(II)<PSB/Avidin product was re-suspended in 1× B&W buffer solution that had the same volume as the starting PSB suspension (0.10-1.0 mL) and kept at about 4° C. until use. Approximately, $6.5 \times 10^4$ Ru(II)<PSB/Avidin beads/µL can thus be estimated, with an assumption of no loss of the beads during the preparation of Ru(II)<PSB/Avidin. FIG. 2B shows a bright green fluorescent image of Ru(II)<PSB/Avidin after the beads reacted with fluorescein biotin, suggesting that a high quality layer of avidin was formed on the surface of Ru(II)<PSB. In contrast, non-specifically adsorbed fluorescein biotin on "bare" Ru(II)<PSB only generate a very weak fluorescent image. The binding capacity of Ru(II)<PSB/Avidin for a biotinylated 23-mer ssDNA (p-ssDNA) was found to have a value of 0.565 nmoles (p-ssDNA)/mg PSB or $1.4 \times 10^8$ p-ssDNA molecules/bead, on the basis of fluorescein biotin titration experiments (see FIG. 10A-10C and Table 1, below).

Example 5

Attaching ssDNA to the Surface of MB and Ru(II)<PSB/Avidin Beads

Probe DNA-MB conjugates. Streptavidin coated magnetic beads (MB), having either a 1.0 µm or a 2.8 µm diameter, were used as the probe DNA carrier. To form probe DNA-MB conjugates, 5.0 µL of 1.0 µm MB, or 10.0 µL of 2.8 µm MB, was first transferred into a 2 mL microcentrifuge tube, then separated from the original suspension with a magnet (Dynal MPC®-S), followed by washing once with 200 µL of "2× B&W buffer" (buffer & wash solution: 10 mM Tris-HCl (pH 7.5), 1.0 mM EDTA,2.0 M NaCl) and twice with 200 µL of 1× B&W buffer before immersing the beads into 100 µL of 2.5 µM biotinylated p-ssDNA and incubating for 30 to 60 minutes with gentle rotation at 40 rpm. The probe DNA-MB conjugates formed were subsequently separated and washed with 200 µL of 1× B&W buffer three times, transferred to a new 2 mL microcentrifuge tube to avoid possible probe DNA adsorption on the wall of the previous tube, and resuspended in 20 µL hybridization buffer. The conjugates produced in this way had a saturated probe DNA coverage of about 2.53 and 1.11 nmoles (p-ssDNA)/mg (beads), or $1.6 \times 10^6$ and $1.0 \times 10^7$ p-ssDNA molecules per bead, for 1.0 µm and 2.8 µm diameter MB, respectively (see FIG. 10A-10C and Table 1).

TABLE 1

| Binding Capacity | | | |
|---|---|---|---|
| Type of Beads | p-ssDNA nmoles per mg Beads | p-ssDNA molecules per Bead | Turning Point |
| 10 µm PSB | 0.565 | $1.4 \times 10^8$ | 20 µL PSB ~29.4 µL of 10 µM p-ssDNA |
| 1.0 µm MB | 2.53 | $1.6 \times 10^6$ | 10 µL MB ~25.3 µL of 10 µM p-ssDNA |
| 2.8 µm MB | 1.11 | $1.0 \times 10^7$ | 20 µL MB ~22.2 µL of 10 µM p-ssDNA |

Target DNA-Ru(II)<PSB/Avidin conjugates. 100 µL of an appropriate concentration of biotinylated t-ssDNA ($1.0 \times 10^{-8}$ to $1.0 \times 10^{-15}$ M), or $1.0 \times 10^{-9}$ M non-complementary-ssDNA (nc-ssDNA) and 2 base pair mismatched-ssDNA (2-bp-m-ssDNA), was added to 25 µL of about $6.5 \times 10^4$ beads/µL Ru(II)<PSB/Avidin in 1× B&W buffer and incubated for 1 hour with gentle mixing at a rotation rate of 20 rpm, washed twice with 200 µL of 1× B&W buffer, centrifuged at 3 k-5 k-10 k rpm for 5 min, and resuspended in 50 µL of the hybridization buffer.

Example 6

DNA Hybridization and ECL Detection

Figure 3:
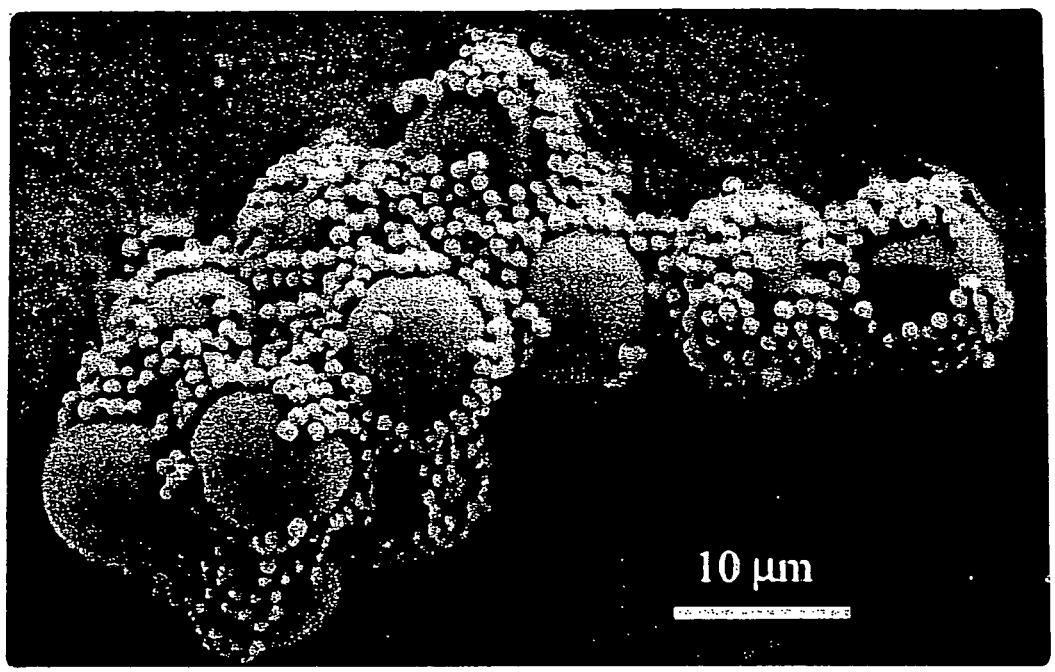
FIG. 3 is a scanning electron micrograph (SEM) image obtained after DNA hybridization between the probe DNA-magnetic bead conjugate (DNA-MB) and the complementary DNA conjugated to an avidin coated polystyrene bead containing $Ru(bpy)_3[B(C_6F_5)_4]_2$ (represented as DNA-Ru(II)<PSB/Avidin). The concentration used for both DNA molecules was 5 μM, and the size of the PSB and the MB was 10 μm and 1.0 μm, respectively.

The newly prepared target DNA-Ru(II)<PSB/Avidin conjugates (Example 5) were transferred into 2 mL centrifuge tubes containing previously formed probe DNA-MB conjugates (Example 5). An appropriate volume of the hybridization buffer was added into the tubes to make a total hybridization solution volume of 200 µL. After gentle mixing at 20 rpm for 1 hour, the probe DNA-MB target DNA-Ru(II)<PSB/Avidin aggregates were magnetically separated from the "solution" containing free unbound Ru(II)<PSB/Avidin beads, washed gently with 200 µL of 1× B&W buffer three times, and carefully transferred into a new centrifuge tube to minimize the possible adsorption of free Ru(II)<PSB/Avidin beads on the wall of the tube. This kind of nonspecific adsorption can produce a significantly high level of background ECL, since, along with the DNA hybridization aggregates, free Ru(II)<PSB/Avidin beads on the wall can also be dissolved in MeCN. The aggregates were finally washed with 200 µL of water, and dissolved in a 0.50 mL of 0.10 M TPrA-0.055 M TFAA-0.10 M (TBA)BF$_4$ MeCN solution for the later ECL measurements. The formation of probe DNA-MB⇌target DNA-Ru(II)<PSB/Avidin aggregates after DNA hybridization can be clearly verified via a SEM image shown in FIG. 3, in which both the probe DNA and the complementary DNA had a concentration of 5 µM, the initial ratio of MB/PSB=29, and the size of the MB and the PSB was 1.0 µm and 10 µm, respectively.

Figure 7A:
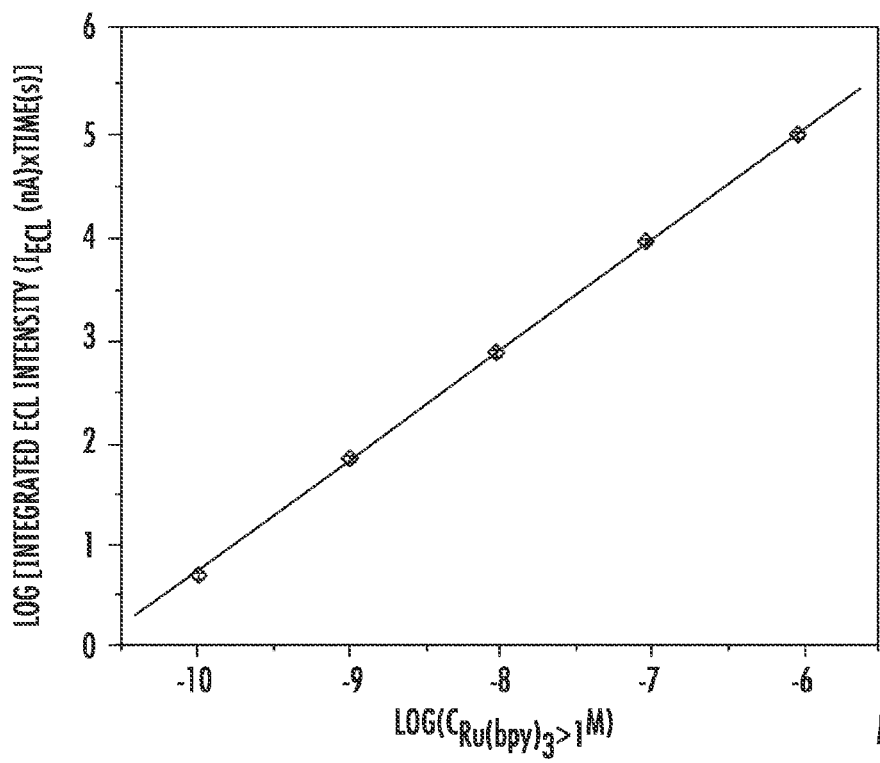
FIG. 7A-B shows the ECL intensity as a function of $Ru(bpy)_3[B(C_6F_5)_4]_2$ concentration FIG. 7A and the number of 10 μm diameter polystyrene beads loaded with $Ru(bpy)_3[B(C_6F_5)_4]_2$ FIG. 7B.
Figure 7B:
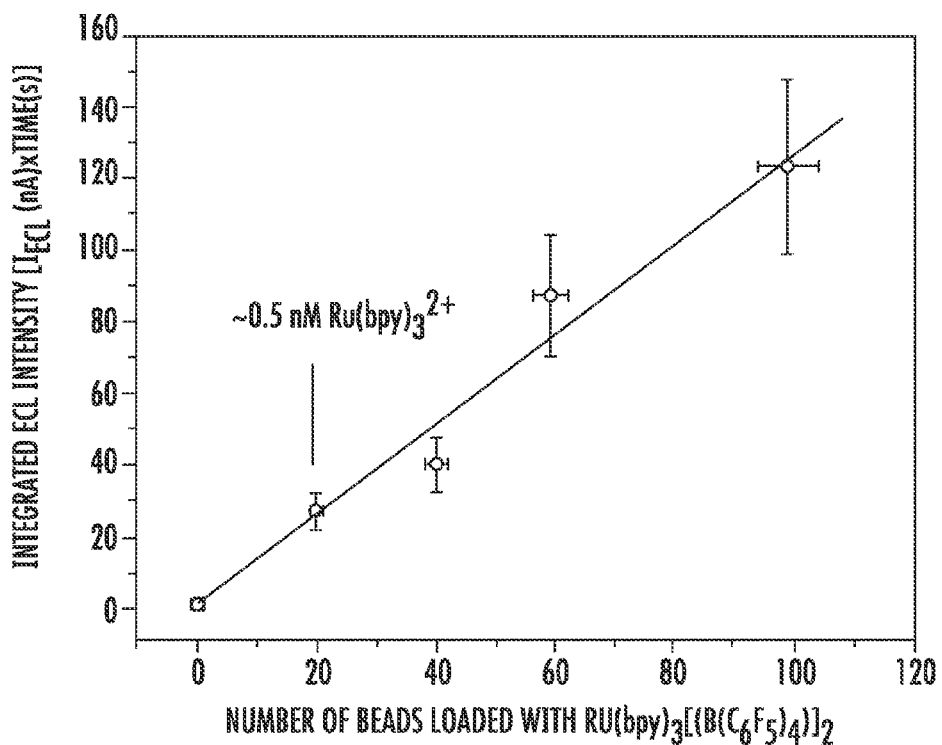

A linear relationship between the ECL intensity and the Ru(bpy)$_3$[B(C$_6$F$_5$)$_4$]$_2$ concentration in a range of 0.10 nM to 1.0 µM was found in 0.10 M TPrA-0.055 M TFAA-0.10 (TBA)BF$_4$ MeCN with the addition of 1% water (FIG. 7B). Under the same experimental conditions, a good correlation between the ECL intensity and the number of 10 µm diameter polystyrene beads loaded with Ru(bpy)$_3$[B(C$_6$F$_5$)$_4$]$_2$ was also observed (FIG. 7B). The beads were dissolved in a 0.50 mL of electrolyte solution, to demonstrate that the polystyrene did not produce or affect the ECL signal. By comparing FIGS. 7B with 7A, it is clear that the light intensity generated from 20 Ru(bpy)$_3^{2+}$ loaded beads is equivalent to that from 0.5 nM Ru(bpy)$_3^{2+}$. The loading capacity of the beads was thus determined to be 7.5×10$^9$ Ru(bpy)$_3$[B(C$_6$F$_5$)$_4$]$_2$ molecules per bead. This result is consistent with the data obtained on the basis of the "bulk beads" ECL measurement.

Figure 8A:
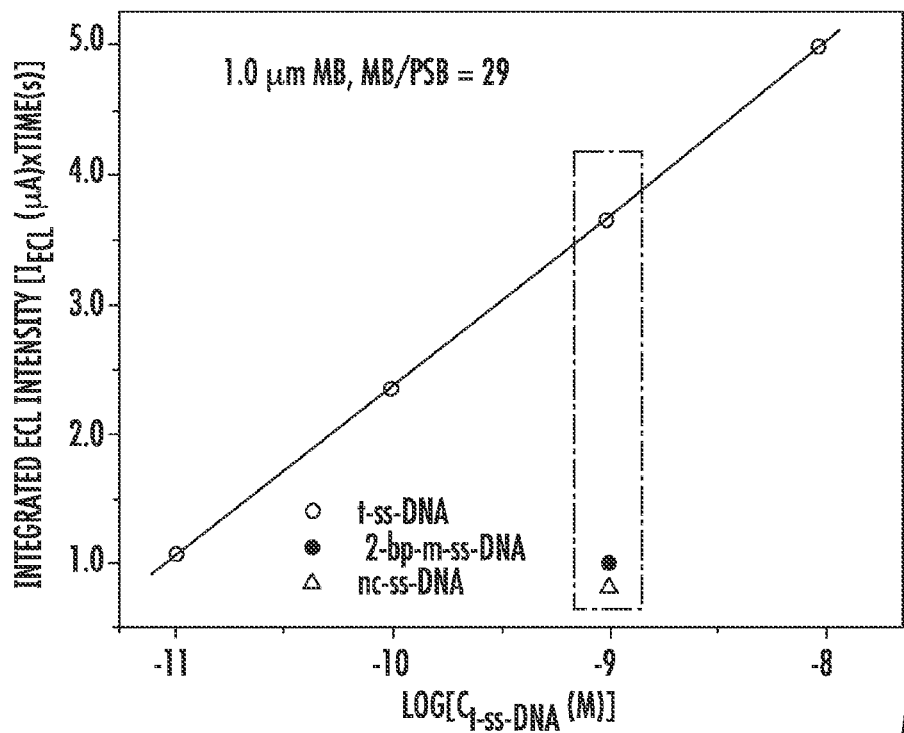
FIG. 8A-B shows the ECL detection of DNA hybridization.
Figure 8B:
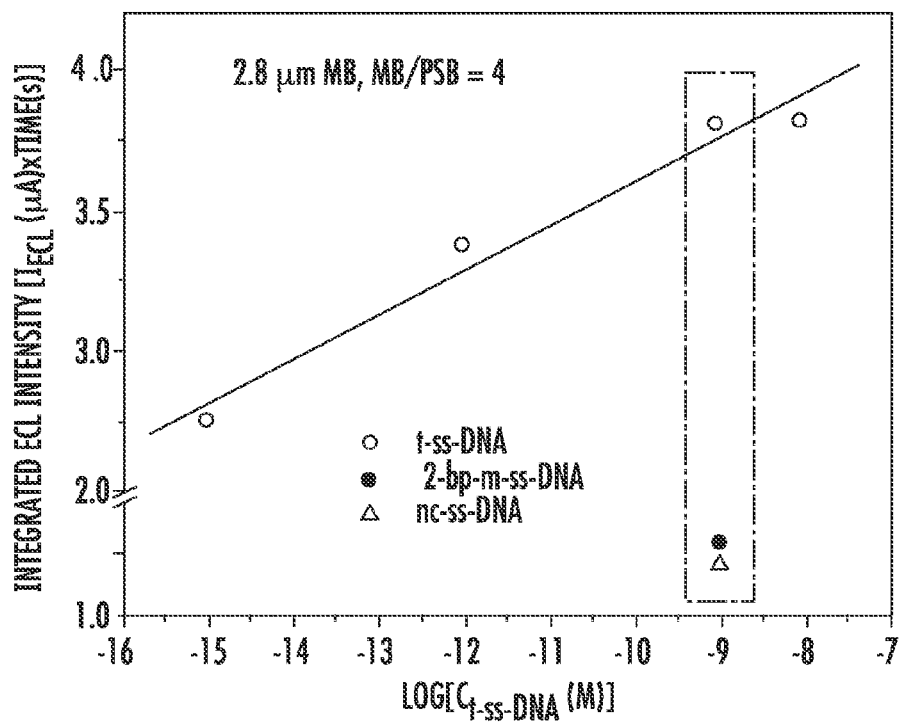

Two sets of experiments were designed for the ECL detection of DNA hybridization. In the first, 1.0 µm diameter MB with a ratio of MB to PSB beads of 29 was used. As shown in FIG. 8A, in this case, the ECL intensity was proportional to the target DNA concentration over a range of 10 µM to 10 nM, and the two-base mismatched 2-bp-m-ssDNA and noncomplementary nc-ssDNA can be readily distinguished from the complementary DNA hybridization. Note that unlike the examples shown in FIGS. 7A and 7B, no water was added to the electrolyte solution because the newly formed MB-PSB conjugates and the microcentrifuge tube already contained sufficient water. Note also that no background subtraction was made for the ECL intensity shown in FIGS. 8A and 8B. By reducing the ratio of MB to PSB, and hence increasing the amplification factor of Ru(bpy)$_3^{2+}$ to t-ssDNA, DNA hybridizations at much lower concentrations of target DNA should be detectable. As demonstrated infra, statistically, one 10 µm diameter PSB can be pulled out with one 2.8 µm diameter MB. As a result, ECL signals related to the DNA hybridization occurred at a very low target DNA concentration and thus can be detectable when the 2.8 µm MB and 10 µm PSB is present at a low ratio. FIG. 8B shows the results of such an example, in which the ratio of 2.8 µm MB/10 µm PSB=4. The t-ssDNA can be detected at a concentration as low as 1.0 fmol. Even under these conditions, the obtained ECL intensity is larger than, and thus distinguishable from, that obtained from the DNA hybridization of 2-bp-m-ssDNA and nc-ssDNA when 1.0 nM of each species was used.

Example 7

Attaching Biotin-PEO-LC-Amine to Carboxylate Polystyrene Beads and the Poisson Distribution Test Biotin-PEO-LC-amine (M.W.=418.6 g/mol) is a water soluble cross-linker with a 22.9 .ANG. polyethylene oxide (PEO) based spacer arm used to reduce the steric hindrance of biotin and avidin interactions (2003-2004 Applications Handbook & Catalog, Pierce Biotechnology, Inc. 2003). Biotin-PEO-LC-amine molecules were covalently attached to the surface of carboxylate polystyrene beads via the formation of amide bond between the primary amine group of the cross-linker and the carboxyl group of the beads in the presence of 0.10 M EDAC-0.10 M NHS in 0.10 M 1-methylimidazole buffer (pH 7). One mL of 5 mM biotin-PEO-LC-amine was used to react with the PSB, separated from 250 µL of 2.6% PSB suspension. The reaction was carried out for 2 hours with a rotation rate of 40 rpm. The cross-linker modified PSB, designated as PSB—CO—NH-LC—PEO-biotin, was subsequently separated and washed with 400 µL of 1× B&W buffer 3 times, re-suspended in 250 µL of 1× B&W buffer, and then kept at 4° C. until use.

Poisson distribution measurements were performed using 10 µm diameter PSB—CO—NH-LC—PEO-biotin beads, with two different sizes of streptavidin/polystyrene coated magnetic beads (1.0 and 2.8 µm in diameter Dynal™ beads). When tens of thousands of PSB—CO—NH-LC—PEO-biotin beads are mixed sufficiently in solution, with the same, or a larger number, of either 1.0 or 2.8 µm magnetic beads, the probability that the PSB—CO—NH-LC—PEO-biotin beads will stick, via the irreversible reaction between the biotin of the PSB and the streptavidin of the MB, can be observed and compared to that predicted for a Poisson distribution. Experimentally, 50 µL of about 6.5×10$^4$ beads/pL PSB—O—NH-LC—PEO-biotin beads (3.3×10$^6$ PSB in total) were diluted with 175 µL of 1× B&W buffer, and transferred to a 2.0 mL microcentrifuge tube containing a known number of streptavidin coated magnetic beads (1.0 µm in diameter) that had been separated magnetically from the manufacturer's original suspension and washed once with 200 µL of 2× B&W buffer. The mixture was immediately shaken and rotated at 40 rpm for 1 hour before the PSB-MB aggregates were magnetically separated from the mixture. The resulting supernatant contained unbound free PSB—CO—NH-LC—PEO-biotin beads, and the number of PSB in the supernatant was determined by optical examination with an inverted microscope. Similar procedures were used to study the Poisson distribution of 2.8 µm MB. However, in this case, only half the amount of the PSB—CO—NH-LC—PEO-biotin beads, i.e., 1.6×10$^6$ beads, were used to react with a known amount of MB.

When a very large number of magnetic beads and polystyrene beads are mixed together, the probability P(m, n) that these two kinds of beads collide and react irreversibly should follow a Poisson distribution and depend on the following two parameters: (a) the initial ratio of magnetic beads to polystyrene beads m, and (b) the number of magnetic beads bound to each polystyrene bead n. For example, if an equal number of MB and PS beads were mixed (m=1), the average number of MB bound to PS should be one. However there will be a distribution, with n=0, 1, 2. . . to lead to this average value. The relationship between P(m, n), m, and n can be described by the Poisson distribution as follows: P(m,n)=e$^{-m}$[m$^{-n}$/n!] n=0, 1, 2, . . . (See, Haight, Handbook of the Poisson Distribution; John Willey & Sons, Inc.: New York, 1967.)

Table 2 lists the P(m,n) values for different values of m and n. With this table and the Poisson distribution test data (provided above), one can estimate the minimum number of magnetic beads required to bind and pull out one single polystyrene bead from the reaction solution. For example, from the number of PSB collected from the supernatant, the percentage of the PSB bound with MB and pulled out magnetically from the reaction mixture can be calculated. A set of "bound PSB %" data with a number of known m values, e.g., m=1, 2, 3, 4, 5. . . , can then be obtained experimentally. If the data fit the theoretical values of P(m, n>j) (Table 2), where m is known from the experiments conducted, j =0, 1, 2, 3. . . , and $$P(m, n > j) = \sum_{i=j+1}^{\tilde{}} P(m, i),$$

then the minimum number of magnetic beads required to bind and pull out one single polystyrene bead must be j+1.

Anal. Chem. 75:5825) in 0.10 M PBS buffer (0.1 M sodium phosphate, 0.15 M sodium chloride) (pH 7.2) (Pierce, Rock-

TABLE 2

| n | m=1 | m=2 | m=3 | m=4 | m=5 | m=6 | m=8 | m=10 | m=12 |
|---|-----|-----|-----|-----|-----|-----|-----|------|------|
| 0 | 0.36788 | 0.13534 | 0.049787 | 0.018316 |  | 0.0024788 |  | 4.5400e−05 | 6.1442e−06 |
| 1 | 0.36788 | 0.27067 | 0.14936 | 0.073263 | 0.033690 | 0.014873 | 0.0026837 |  | 7.3731e−05 |
| 2 | 0.18394 | 0.27067 | 0.22404 | 0.14653 | 0.084224 | 0.044618 | 0.010735 | 0.0022700 | 0.00044238 |
| 3 | 0.061313 | 0.18045 | 0.22404 | 0.19537 | 0.14037 | 0.089235 | 0.028626 | 0.0075667 | 0.0017695 |
| 4 | 0.015328 | 0.090224 | 0.16803 | 0.19537 | 0.17547 | 0.13385 | 0.057252 | 0.018917 | 0.0053086 |
| 5 |  | 0.036089 | 0.10082 | 0.15629 | 0.17547 | 0.16062 | 0.091604 | 0.037833 | 0.012741 |
| ... | ... | ... | ... | ... | ... | ... | ... | ... | ... |
| Sum | 1 | 1 | 1 | 1 | 1 | 1 | 1 | 1 | 1 |

Figure 9:
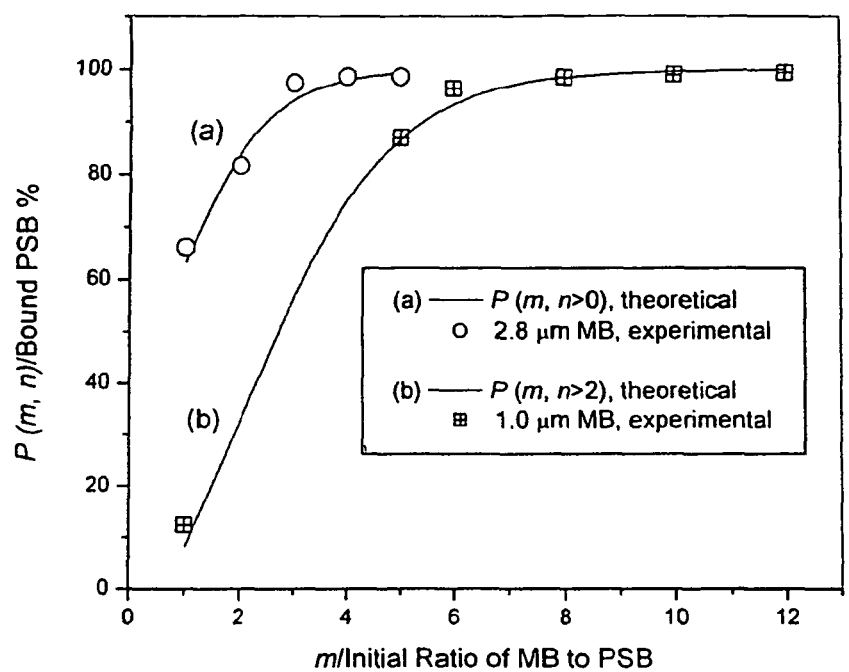
FIG. 9 shows a Poisson distribution test using (a) 2.8 μm and (b) 1.0 μm diameter streptavidin coated MB reacted with 10 μm diameter biotinylated PSB. The "Bound PSB %" was calculated from the number of PSB found in the supernatant after the magnetic separation of MB-PSB conjugates from the reaction media.

FIG. 9 shows two examples of such a test. In the first example (FIG. 9a), 2.8 μm MB and 10 μm PSB were used, and a minimum binding ratio of MB/PSB=1 can be deduced. In the second example (FIG. 9b), instead of 2.8 μm MB, 1.0 μm MB was used to react with 10 μm PSB. In this case a higher minimum MB to PSB binding ratio of 3 was obtained. These binding ratios can be utilized to optimize experimental conditions for the DNA hybridization between MB and PSB, so that a minimum target DNA concentration could be detected.

Example 8

Loading of Two Aromatic Hydrocarbons, DPA and Rubrene, into Polystyrene Bead

Figure 11B:
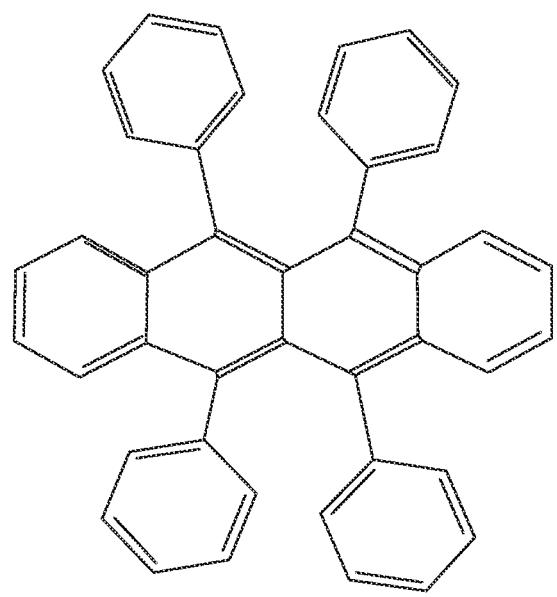
FIG. 11A-B shows the molecular structures of DPA FIG. 11A and RUB FIG. 11B.
Figure 11A:
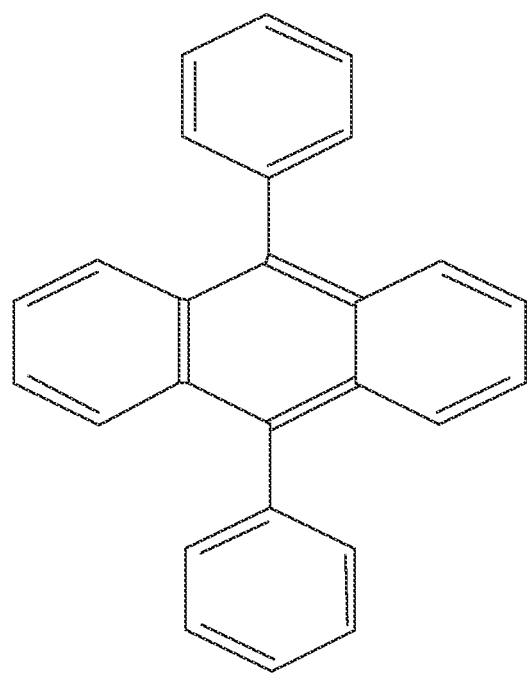
Figure 12:
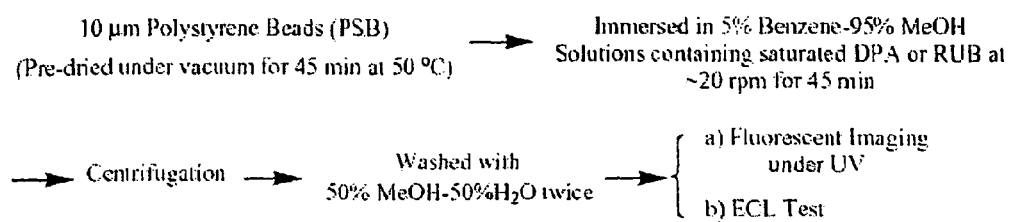
FIG. 12 is flow chart depicting the steps in a procedure for loading aromatic hydrocarbons into polystyrene beads.

In addition to $Ru(bpy)_3[B(C_6F_5)_4]_2$, aromatic hydrocarbons, e.g., 9,10-diphenylanthracene (DPA, FIG. 11A) and rubrene (RUB, FIG. 11B), were also loaded into polystyrene beads (PSB). As a result, ECL labels with different emission wavelengths were obtained. The loading procedures were similar to those used for $Ru(bpy)_3[B(C_6F_5)_4]_2$ entrapping, except that 5% THF-95% MeOH "swelling solvent" was replace by 5% benzene-95% MeOH so that the two aromatic hydrocarbons are sufficiently soluble in benzene contained solvent. FIG. 12 summarizes the loading procedures.

Figures 13A, 13B, 13C:
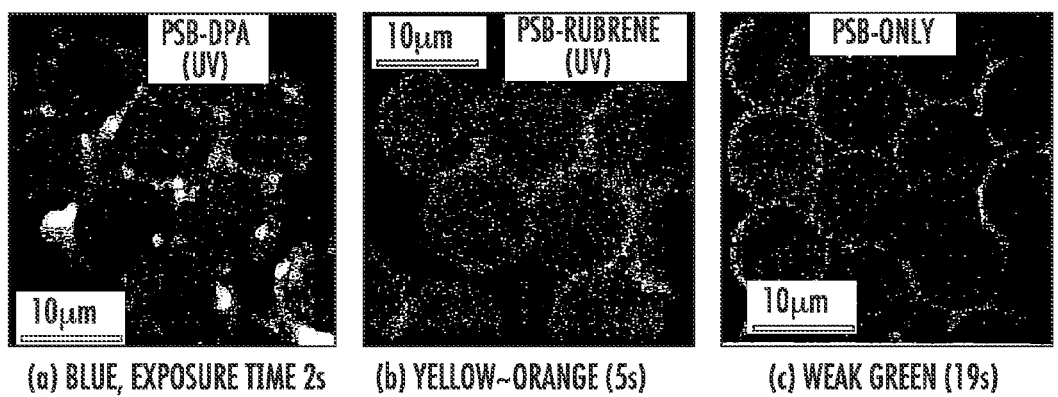
FIG. 13A-C shows fluorescent images of FIG. 13A DPA loaded PSB.

The entrapping of DPA and RUB into PSB was visually verified using fluorescent imaging with UV light excitations. As shown in FIGS. 13A and 13B, strong blue and yellow to orange fluorescent images are observed for DPA and RUB loaded PSB, respectively. In contrast, PSB with no aromatic hydrocarbon showed weak green fluorescence (FIG. 13C).

Figure 14A:
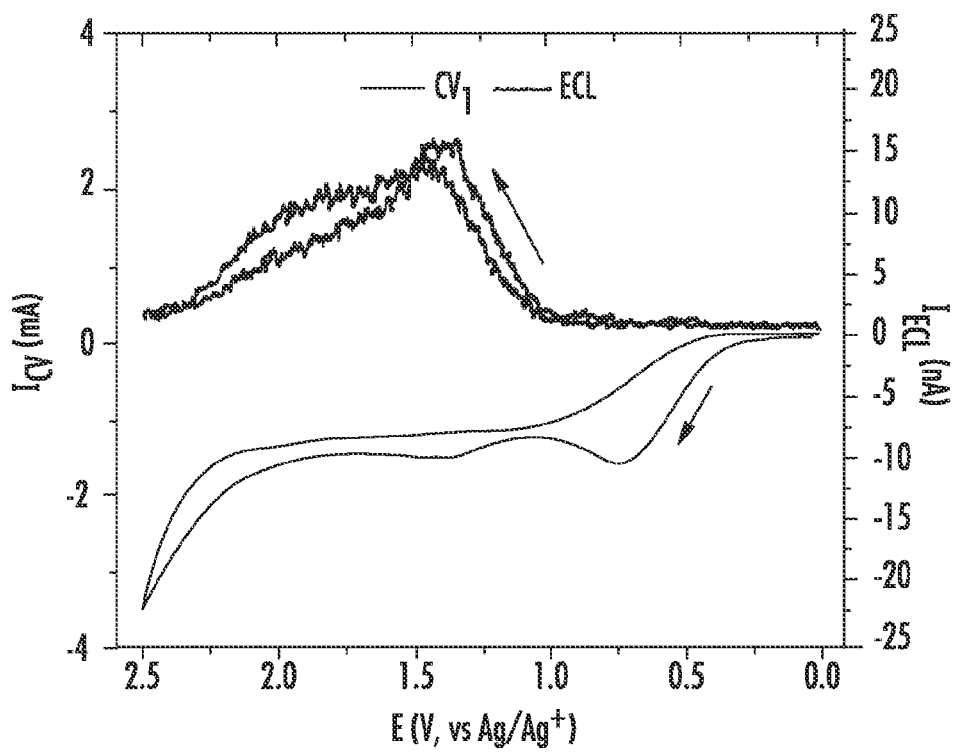
FIG. 14A-B shows the CV and ECL behavior of FIG. 14A DPA loaded PSB dissolved in MeCN and FIG. 14B 0.25 mM DPA acetonitrile solution using TPrA as a coreactant.
Figure 14B:
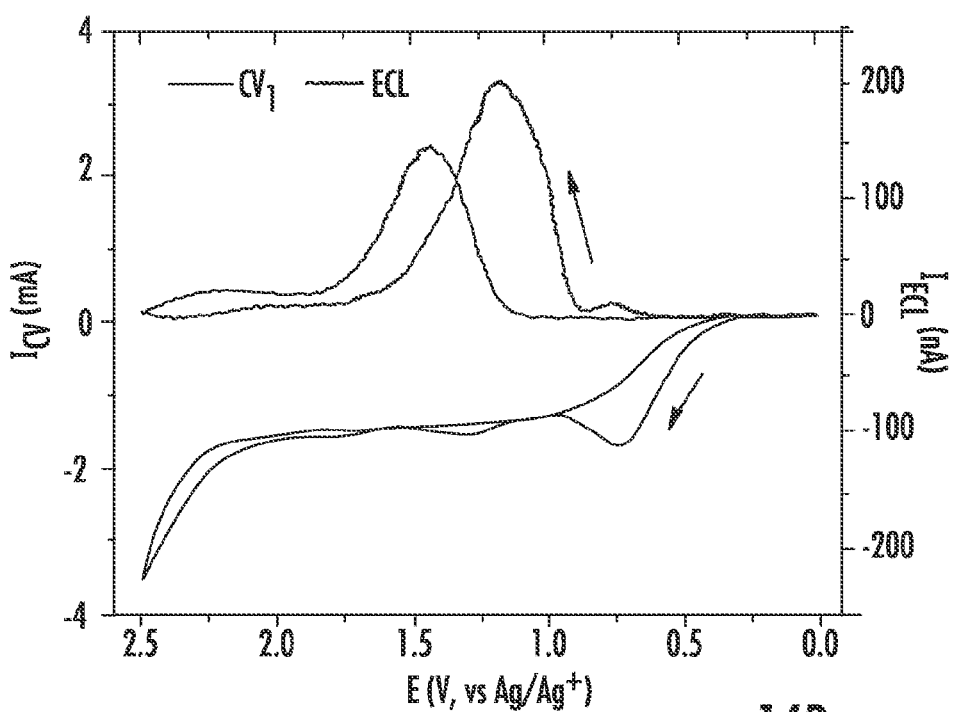
Figure 15A:
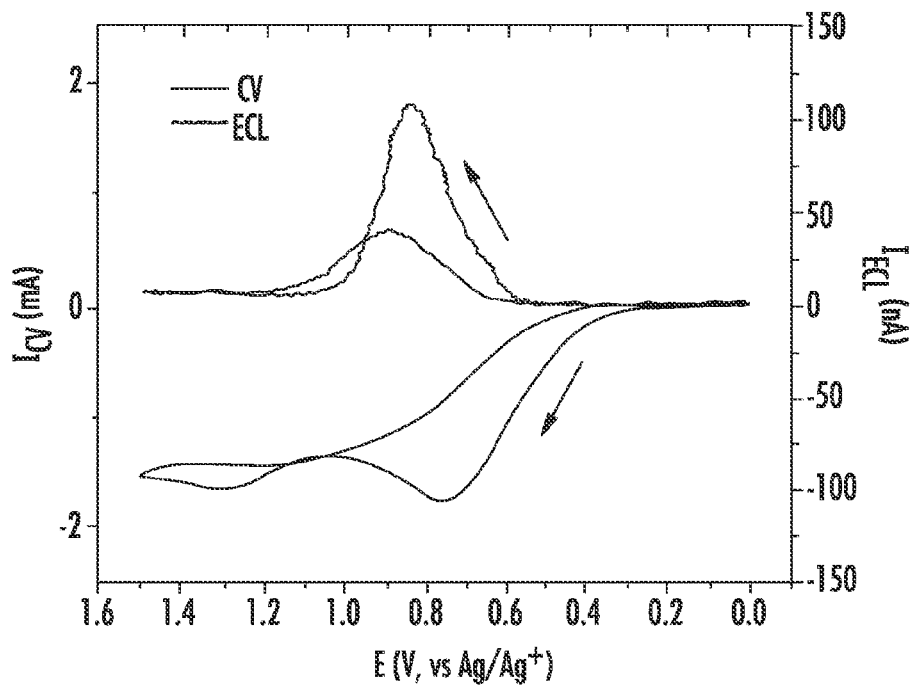
FIG. 15A-B shows the CV and ECL behavior of FIG. 15A RUB loaded PSB dissolved in MeCN and FIG. 15B 35 μM RUB acetonitrile solution using TPrA as a coreactant.
Figure 15B:
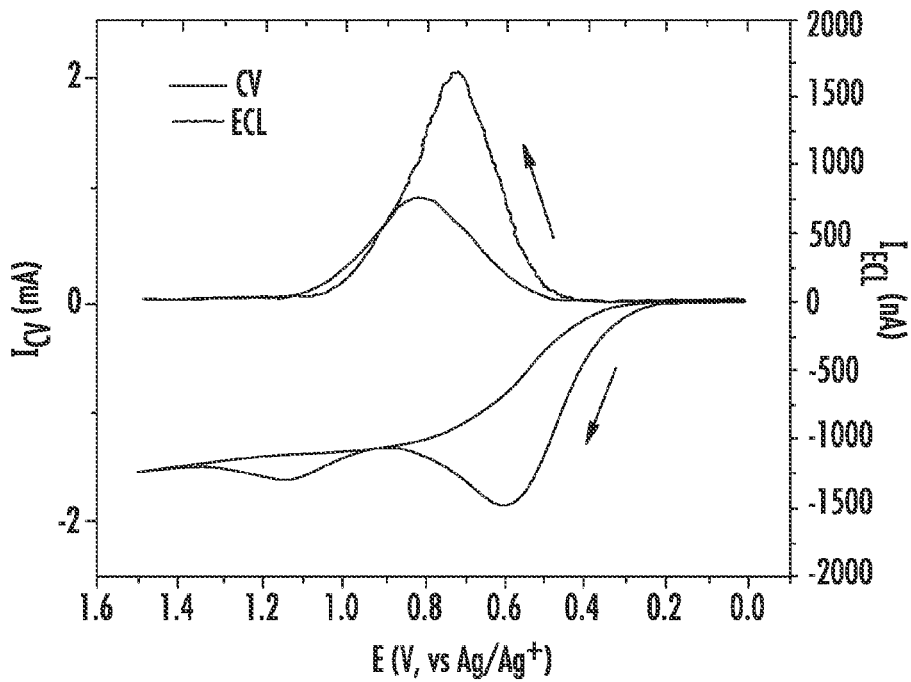

A loading capacity of $7.5 \times 10^9$ DPA molecules per bead or $4.0 \times 10^8$ RUB molecules per bead was estimated on the basis of the ECL data obtained from the DPA or RUB loaded PSB dissolved in MeCN and a standard DPA or RUB solution using tri-propylamine (TPrA) as a coreactant. FIG. 14 shows the CV and ECL behavior of FIG. 14A DPA loaded PSB dissolved in MeCN and FIG. 14B 0.25 mM DPA acetonitrile solution using TPrA as a coreactant. The CV and ECL behavior of RUB loaded PSB dissolved in MeCN and 35 μM RUB acetonitrile solution using TPrA as a coreactant is shown in FIGS. 15A and 15B, respectively.

Example 9

ECL Detection of C Reactive Protein (CRP)

Ru(II)<PSB/Avidin←Anti-CRP conjugates were prepared as follows: 0.100-0.500 mL of Ru(II)<PSB/Avidin ($6.5 \times 10^4$ beads/μL) (see Example 4) were mixed with 1 mL of 2.0 mg/mL biotinylated anti-CRP (Miao and Bard, 2003, ford, Ill.) with a rotation rate of 25 rpm at room temperature for 1 hour. The newly formed conjugates were collected by centrifugation, washed with 1× B&W buffer three times (see Example 4), and resuspended in 1 mL of 2% bovine serum albumin (BSA)/0.10 M PBS (pH 7.2) solution for 30 minutes. After centrifugation and washing (as above), the conjugates were suspended in a suitable volume (0.100-0.500 mL) of 0.10 M PBS (pH 7.2) buffer solution and kept at 4° C. until use.

MB←Anti-CRP conjugates were prepared as follows: 0.100-0.500 mL of 2.8 μm diameter streptavidin-coated magnetic beads (MB, $6.5 \times 10^5$ beads/up were magnetically separated and washed once with 1 mL of 2× B&W buffer and twice with 1 mL of 1× B&W buffer, followed by mixing with 1.5 mL of 2.0 mg/mL biotinylated anti-CRP in 0.10 M PBS buffer (pH 7.2) at a rotation rate of 25 rpm at room temperature for 1 hour. The newly formed MB←anti-CRP conjugates were washed with 1 mL of 1× B&W buffer 3 times, resuspended in a suitable volume (0.100-0.500 mL) of 0.10 M PBS (pH 7.2) buffer solution, and stored at 4° C. until use.

Sandwich-Type Ru(II)<PSB/Avidin←Anti-CRP<CRP>MB←Anti-CRP conjugates were formed as follows: 20 μL of Ru(II)<PSB/Avidin←Anti-CRP Conjugates ($1.3 \times 10^6$ PSB in total) and 20 μL of MB←Anti-CRP Conjugates ($1.3 \times 10^7$ MB in total) were gently mixed with a CRP sample in 200 μL of 0.10 M PBS (pH 7.2) buffer solution at room temperature for 2 hours. The sandwich-type conjugates were magnetically separated from the mixture solution and washed 3 times with 200 μL of 1× B&W buffer. The conjugates were then transferred, with a small volume of PBS buffer, to a new 2 mL centrifuge tube, so that possible adsorption of free Ru(II)<PSB/Avidin←Anti-CRP on the wall of the old tube was minimized (cf. Example 6). Finally, the "magnetic conjugates" were separated from the solution with a magnet.

Figure 16:
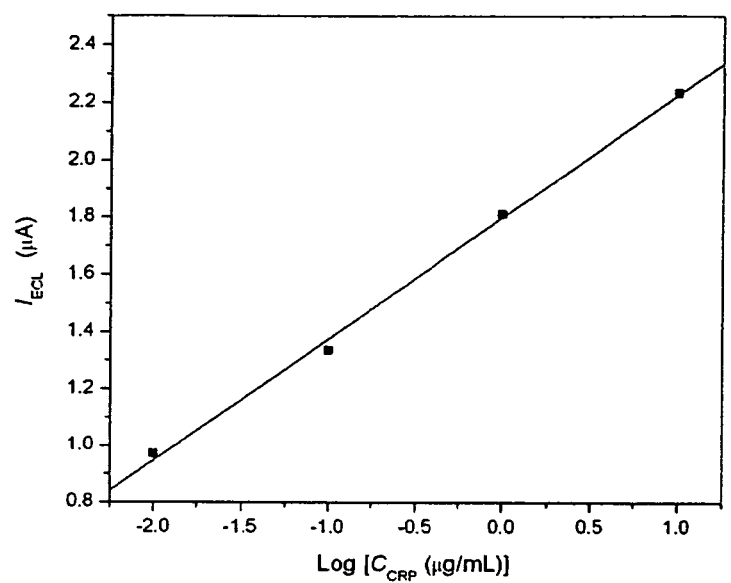
FIG. 16 shows the relationship between ECL signal and concentration of C reactive protein (CRP).

CRP was detected by ECL. The obtained sandwich-type conjugates were dissolved in 0.500 mL of 0.10 M TPrA-0.055 TFAA-0.10 M $(TBA)BF_4$ MeCN solution, and the ECL experiments were carried out at a 2.2 mm diameter Pt electrode using cyclic voltammetry with a scanning potential window between 0 and 2.8 V vs. Ag/Ag$^+$ (10 mM AgBF$_4$ in 0.10 M $(TBA)BF_4$ MeCN) at a scan rate of 50 mV/s. As expected, the profiles of CV and ECL obtained from the sandwich-type conjugates were very similar to those shown in FIGS. 4a and c, since, in both cases, the "reactive species", $Ru(bpy)_3^{2+}$ and TPrA, were the same. As shown in FIG. 16, the ECL intensity (the average of the forward scan peak intensity and the reverse scan peak intensity) is linearly proportional to the CRP concentration over the range of 0.010-10 µg/mL.

All references cited herein are incorporated herein by reference in their entirety. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of the present methods and compositions can be made without departing from their spirit and scope, as will be apparent to those skilled in the art. The specific embodiments described herein are offered by way of example only and are not meant to be limiting in any way. It is intended that the specification and examples be considered as exemplary only.

What is claimed is:

1. A method of detecting an analyte of interest in a sample, comprising
   (a) forming a composition comprising:

$(A)_k(B)_u(C)(D)_x$ wherein A is an electrogenerated chemiluminescent (ECL) moiety which can be induced to repeatedly emit electromagnetic radiation by direct exposure to an electrochemical energy source; and the ECL moiety is soluble in organic solvent and insoluble in aqueous solvent;
   B is a synthetic organic polymer bead comprising a plurality of the ECL moieties entrapped within its interior; and B is either linked to the analyte of interest or linked to a first specific binding partner of the analyte of interest;
   C is the sample which may contain the analyte of interest; and
   D is a magnetizable bead which is either linked to the analyte of interest or linked to a second specific binding partner of the analyte of interest;
   wherein k, u, and x are each an integer equal to or greater than 1;
   (b) separating a complex comprising A, B, D and the analyte of interest from other components of the composition;
   (c) inducing the ECL moiety in the complex to repeatedly emit electromagnetic radiation by directly exposing the moiety to electrochemical energy; and
   (d) detecting the emitted electromagnetic radiation and thereby detecting the presence of the analyte of interest, provided that B and D are not both linked to the analyte of interest.

2. The method of claim 1, wherein B is linked to the first specific binding partner; and D is linked to the second specific binding partner.

3. The method of claim 1, wherein the analyte of interest is a protein.

4. The method of claim 3, wherein the first specific binding partner is an antibody, a part of an antibody, or a binding protein; and the second specific binding partner is an antibody, a part of an antibody, or a binding protein.

5. The method of claim 1, wherein the analyte of interest is a nucleic acid.

6. The method of claim 5, wherein the first specific binding partner is a nucleic acid; and the second specific binding partner is a nucleic acid.

7. The method of claim 5, wherein the first specific binding partner is an oligonucleotide; the second specific binding partner is an oligonucleotide.

8. The method of claim 1, wherein the synthetic organic polymer bead comprises a compound chosen from polystyrene, polyacrylic, nylon, polymethacrylate, polyacrylamide, polyacrylonitrile, PVDF, poly(lactide-co-ethylene glycol), and polyolefins.

9. The method of claim 1, wherein the ECL moiety comprises a metal ion selected from osmium or ruthenium and at least one polydendate ligand.

10. The method of claim 1, wherein the ECL moiety comprises bis(2,2'-bipyridyl)-ruthenium(II) or tris(2,2'-bipyridyl)ruthenium(II).

11. The method of claim 1, wherein the composition further comprises an amine ECL coreactant.

12. The method of claim 11, wherein the amine ECL coreactant comprises tripropylamine (TPrA), piperazine-1, 4-bis(2-ethanesulfonic acid) (PIPES), N,N,N',N'-tetrapropyl-1,3-diaminopropane or a mixture thereof.

13. The method of claim 11, wherein the synthetic organic polymer bead is a polystyrene bead; the amine ECL coreactant comprises tripropylamine; and the ECL moiety comprises bis(2,2'-bipyridyl)-ruthenium(II) or tris(2,2'-bipyridyl) ruthenium(II).

14. The method of claim 11, wherein each ECL moiety comprises $Ru(bpy)_3[B(C_6F_5)_4]_2$; and the amine ECL coreactant comprises tripropylamine.

15. The method of claim 1, wherein the analyte of interest is a protein; the first specific binding partner is an antibody, a part of an antibody, or a binding protein; and the second specific binding partner is an antibody, a part of an antibody, or a binding protein; and the ECL moiety comprises a ruthenium ion and three bidentate ligands.

16. The method of claim 15, wherein the ECL moieties comprise $Ru(bpy)_3[B(C_6F_5)_4]_2$.

17. The method of claim 1, wherein the analyte of interest is a nucleic acid; the first specific binding partner is an oligonucleotide; and the second specific binding partner is an oligonucleotide; and the ECL moiety comprises a ruthenium ion and three bidentate ligands.

18. A method of detecting an analyte of interest in a sample, comprising
   (a) forming a composition comprising:

$(A)_k(B)_u(C)(D)_x$ wherein A is an ECL moiety which can be induced to repeatedly emit electromagnetic radiation by direct exposure to an electrochemical energy source; and the ECL moiety is soluble in organic solvent and insoluble in aqueous solvent;
   B is a polystyrene bead, which is either linked to the analyte of interest or linked to a first specific binding partner of the analyte of interest; wherein a plurality of the ECL moieties are entrapped within the polystyrene bead;
   C is the sample which may contain the analyte of interest; and D is a magnetic polymeric bead, which is either linked to the analyte of interest or linked to a second specific binding partner of the analyte of interest;

wherein u and x are each an integer equal to or greater than 1; k is an integer greater than or equal to 2; and provided that B and D are not both linked to the analyte of interest;

(b) separating a complex comprising A, B, D and the analyte of interest from other components of the composition;

(c) dissolving B from the separated complex in an organic solvent;

(d) inducing the ECL moieties from the dissolved B to repeatedly emit electromagnetic radiation by exposing the ECL moieties to electrochemical energy in the presence of an ECL coreactant, which comprises tertiary amine; and (e) detecting the emitted electromagnetic radiation.

19. The method of claim 18, wherein the ECL moieties comprise bis(2,2'-bipyridyl)ruthenium(II) or tris(2,2'-bipyridyl) ruthenium(II); the ECL coreactant comprises tripropylamine; and the analyte of interest is a protein or a nucleic acid molecule.

20. The method of claim 18, wherein the first specific binding partner is an antibody, nucleic acid, receptor or enzyme.

21. The method of claim 1, wherein the ECL moieties comprise a ruthenium ion and at least one polydendate ligand; the synthetic organic polymer bead is a polystyrene bead; the magnetizable bead is a magnetic polymeric bead; and the composition further comprises an amine ECL coreactant.

* * * * *